US011921096B2

(12) United States Patent
Sherwood et al.

(10) Patent No.: US 11,921,096 B2
(45) Date of Patent: Mar. 5, 2024

(54) FLUID ANALYSIS SYSTEM

(71) Applicant: REGENTS OF THE UNIVERSITY OF MINNESOTA, Minneapolis, MN (US)

(72) Inventors: Gregory J. Sherwood, White Bear Lake, MN (US); Justin Theodore Nelson, Vadnais Heights, MN (US); Raia Colette Finc, Shoreview, MN (US); Michael J. Lyden, Shoreview, MN (US); John M. Darst, Oakdale, MN (US); Michael Mathias Freking, Arden Hills, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 431 days.

(21) Appl. No.: 17/012,642

(22) Filed: Sep. 4, 2020

(65) Prior Publication Data
US 2021/0072208 A1   Mar. 11, 2021

Related U.S. Application Data

(60) Provisional application No. 62/898,155, filed on Sep. 10, 2019.

(51) Int. Cl.
*G01N 33/00* (2006.01)
*G01N 27/447* (2006.01)
*G01N 27/70* (2006.01)

(52) U.S. Cl.
CPC ... *G01N 33/0008* (2013.01); *G01N 27/44765* (2013.01); *G01N 27/70* (2013.01); *G01N 33/0034* (2013.01)

(58) Field of Classification Search
CPC ......... G01N 33/0008; G01N 27/44765; G01N 27/70
(Continued)

(56) References Cited

U.S. PATENT DOCUMENTS 5,704,368 A   1/1998   Asano et al.
5,834,626 A   11/1998  De Castro et al.
(Continued)

FOREIGN PATENT DOCUMENTS

CN   1301342    6/2001
CN   107076693  9/2017
(Continued)

OTHER PUBLICATIONS

"International Preliminary Report on Patentability," for PCT Application No. PCT/US2020/049395 dated Mar. 24, 2022 (11 pages).
(Continued)

*Primary Examiner* — Daniel S Larkin
(74) *Attorney, Agent, or Firm* — Pauly, DeVries Smith & Deffner LLC

(57) ABSTRACT

Embodiments herein relate to breath analysis system. In an embodiment, a gas measurement device is included having a housing defining an interior volume. The housing can include a fluid ingress port, a fluid egress port, a bottom wall, and a circuit board disposed within the interior volume. The circuit board can include a first side and a second side, where the first side of the circuit board faces inward toward the interior volume. The circuit board can include a plurality of gas sensors disposed on the first side of the circuit board and a plurality of conductive pads disposed on the second side of the circuit board, wherein a plurality of electrical contacts contact the conductive pads when the circuit board is seated within the housing. Other embodiments are also included herein.

16 Claims, 11 Drawing Sheets

(58) Field of Classification Search
USPC .......................................................... 73/23.3
See application file for complete search history.

(56) References Cited

U.S. PATENT DOCUMENTS

| | | |
|---|---|---|
| 6,085,576 A | 7/2000 | Sunshine et al. |
| 6,149,624 A | 11/2000 | McShane |
| 6,192,168 B1 | 2/2001 | Feldstein et al. |
| 6,248,078 B1 | 6/2001 | Risby et al. |
| 6,312,390 B1 | 11/2001 | Phillips |
| 6,480,734 B1 | 11/2002 | Zhang et al. |
| 6,599,253 B1 | 7/2003 | Baum et al. |
| 6,712,770 B2 | 3/2004 | Lin et al. |
| 6,726,637 B2 | 4/2004 | Phillips |
| 6,781,690 B2 | 8/2004 | Armstrong et al. |
| 6,955,652 B1 | 10/2005 | Baum et al. |
| 6,978,182 B2 | 12/2005 | Mazar et al. |
| 7,032,431 B2 | 4/2006 | Baum et al. |
| 7,123,359 B2 | 10/2006 | Armstrong et al. |
| 7,177,686 B1 | 2/2007 | Turcott et al. |
| 7,426,848 B1 | 9/2008 | Li et al. |
| 7,459,312 B2 | 12/2008 | Dai et al. |
| 7,704,214 B2 | 4/2010 | Abraham-Fuchs et al. |
| 7,809,441 B2 | 10/2010 | Kane et al. |
| 7,871,572 B2 | 1/2011 | Kim et al. |
| 7,972,277 B2 | 7/2011 | Oki et al. |
| 7,992,422 B2 | 8/2011 | Leddy et al. |
| 8,043,860 B2 | 10/2011 | Lefebvre et al. |
| 8,080,206 B2 | 12/2011 | Leddy et al. |
| 8,113,063 B2 | 2/2012 | Nakaso |
| 8,124,419 B2 | 2/2012 | Brahim et al. |
| 8,153,439 B2 | 4/2012 | Zamborini et al. |
| 8,154,093 B2 | 4/2012 | Bradley et al. |
| 8,157,730 B2 | 4/2012 | LeBoeuf et al. |
| 8,222,041 B2 | 7/2012 | Ren et al. |
| 8,366,630 B2 | 2/2013 | Haick et al. |
| 8,481,324 B2 | 7/2013 | Haick et al. |
| 8,494,606 B2 | 7/2013 | Debreczeny et al. |
| 8,529,459 B2 | 9/2013 | Malker et al. |
| 8,597,953 B2 | 12/2013 | Haick |
| 8,747,325 B2 | 6/2014 | Bacal et al. |
| 8,828,713 B2 | 9/2014 | Ren et al. |
| 8,835,984 B2 | 9/2014 | Ren et al. |
| 8,848,189 B2 | 9/2014 | Atkin et al. |
| 8,955,367 B2 | 2/2015 | Gouma et al. |
| 9,011,779 B1 | 4/2015 | Anglin, Jr. et al. |
| 9,029,168 B2 | 5/2015 | Mannoor et al. |
| 9,103,775 B2 | 8/2015 | Bradley et al. |
| 9,147,851 B1 | 9/2015 | Bartsch et al. |
| 9,315,848 B2 | 4/2016 | Haick et al. |
| 9,316,637 B2 | 4/2016 | Ren et al. |
| 9,324,825 B2 | 4/2016 | Accardi et al. |
| 9,366,664 B2 | 6/2016 | Anglin, Jr. et al. |
| 9,513,244 B2 | 12/2016 | Koester |
| 9,618,476 B2 | 4/2017 | Goldsmith |
| 9,765,395 B2 | 9/2017 | Goldsmith |
| 10,191,005 B2 | 1/2019 | Koester |
| 2002/0123749 A1 | 9/2002 | Jain et al. |
| 2002/0142477 A1 | 10/2002 | Lewis et al. |
| 2003/0051733 A1 | 3/2003 | Kotmel et al. |
| 2004/0040841 A1 | 3/2004 | Gonzalez-Martin et al. |
| 2005/0065446 A1 | 3/2005 | Talton |
| 2006/0130557 A1 | 6/2006 | Leddy et al. |
| 2006/0263255 A1 | 11/2006 | Han et al. |
| 2006/0270940 A1 | 11/2006 | Tsukashima et al. |
| 2007/0048181 A1 | 3/2007 | Chang et al. |
| 2007/0062255 A1* | 3/2007 | Talton .................. G01N 33/497 73/23.3 |
| 2007/0083094 A1 | 4/2007 | Colburn et al. |
| 2007/0167853 A1 | 7/2007 | Melker et al. |
| 2007/0229818 A1 | 10/2007 | Duan et al. |
| 2008/0021339 A1 | 1/2008 | Gabriel et al. |
| 2008/0146890 A1 | 6/2008 | LeBoeuf et al. |
| 2008/0183910 A1 | 7/2008 | Natoli et al. |
| 2008/0317636 A1 | 12/2008 | Brahim et al. |
| 2009/0054799 A1 | 2/2009 | Vrtis et al. |
| 2009/0112115 A1 | 4/2009 | Huang et al. |
| 2010/0024533 A1 | 2/2010 | Kimura et al. |
| 2010/0085067 A1 | 4/2010 | Gabriel et al. |
| 2010/0137733 A1 | 6/2010 | Wang et al. |
| 2010/0188069 A1 | 7/2010 | Ren et al. |
| 2010/0198521 A1 | 8/2010 | Haick |
| 2010/0216175 A1 | 8/2010 | Melker et al. |
| 2010/0273665 A1 | 10/2010 | Haick et al. |
| 2011/0015872 A1 | 1/2011 | Haick et al. |
| 2011/0017587 A1 | 1/2011 | Zhamu et al. |
| 2011/0138904 A1 | 6/2011 | Nakaso |
| 2011/0143962 A1 | 6/2011 | Chaubron |
| 2011/0269632 A1 | 11/2011 | Haick et al. |
| 2011/0283770 A1 | 11/2011 | Hok |
| 2012/0028820 A1 | 2/2012 | Rhodes et al. |
| 2012/0111093 A1 | 5/2012 | Brahim et al. |
| 2012/0126111 A1 | 5/2012 | Chaubron et al. |
| 2012/0156099 A1 | 6/2012 | Zhong et al. |
| 2012/0166095 A1 | 6/2012 | Potyrailo et al. |
| 2012/0203081 A1 | 8/2012 | LeBoeuf et al. |
| 2012/0226111 A1 | 9/2012 | LeBoeuf et al. |
| 2012/0226112 A1 | 9/2012 | LeBoeuf et al. |
| 2012/0245434 A1 | 9/2012 | Haick et al. |
| 2012/0245854 A1 | 9/2012 | Haick et al. |
| 2012/0326092 A1 | 12/2012 | Haick et al. |
| 2013/0034190 A1 | 2/2013 | Tan et al. |
| 2013/0034910 A1 | 2/2013 | Haick et al. |
| 2013/0059758 A1 | 3/2013 | Haick et al. |
| 2013/0102018 A1 | 4/2013 | Schentag et al. |
| 2013/0143247 A1 | 6/2013 | Haick et al. |
| 2013/0150261 A1 | 6/2013 | Haick et al. |
| 2013/0171733 A1 | 7/2013 | Haick et al. |
| 2013/0211207 A1 | 8/2013 | Joseph et al. |
| 2013/0211852 A1 | 8/2013 | Roizen et al. |
| 2013/0236981 A1 | 9/2013 | Haick et al. |
| 2013/0253358 A1 | 9/2013 | Phillips |
| 2013/0289368 A1 | 10/2013 | Covington et al. |
| 2013/0334579 A1 | 12/2013 | Accardi et al. |
| 2014/0018691 A1 | 1/2014 | McNeill |
| 2014/0051956 A1 | 2/2014 | Dalene et al. |
| 2014/0145735 A1 | 5/2014 | Koester |
| 2014/0275597 A1 | 9/2014 | Zhang et al. |
| 2014/0294675 A1 | 10/2014 | Melker et al. |
| 2015/0013429 A1 | 1/2015 | Atkin et al. |
| 2015/0038378 A1 | 2/2015 | Cheng et al. |
| 2015/0044710 A1 | 2/2015 | Dasgupta et al. |
| 2015/0065365 A1 | 3/2015 | Ahmad |
| 2015/0257676 A1 | 9/2015 | Fries |
| 2015/0307936 A1 | 10/2015 | Goldsmith |
| 2015/0309018 A1 | 10/2015 | Goldsmith |
| 2015/0335266 A1 | 11/2015 | Cormier |
| 2015/0338390 A1 | 11/2015 | Anglin, Jr. et al. |
| 2016/0025675 A1 | 1/2016 | Goldsmith |
| 2016/0054312 A1 | 2/2016 | Goldsmith |
| 2016/0109440 A1 | 4/2016 | Sherwood et al. |
| 2016/0116431 A1 | 4/2016 | Accardi et al. |
| 2016/0209436 A1* | 7/2016 | Wu ........................ G01N 33/98 |
| 2016/0231309 A1 | 8/2016 | Ahmad et al. |
| 2017/0014043 A1 | 1/2017 | McDonnell |
| 2017/0042435 A1 | 2/2017 | Vermeulen et al. |
| 2017/0053068 A1 | 2/2017 | Pillai et al. |
| 2017/0251952 A1 | 9/2017 | Harshman et al. |
| 2017/0254817 A1 | 9/2017 | Grafman et al. |
| 2017/0307562 A1 | 10/2017 | Goldsmith |
| 2017/0360337 A1 | 12/2017 | Sherwood et al. |
| 2017/0361599 A1 | 12/2017 | Lerner et al. |
| 2017/0365474 A1 | 12/2017 | Pan et al. |
| 2017/0365477 A1 | 12/2017 | Pan et al. |
| 2017/0365562 A1 | 12/2017 | Pan et al. |
| 2018/0037952 A1 | 2/2018 | Goldsmith |
| 2018/0037985 A1 | 2/2018 | Myers et al. |
| 2018/0110444 A1 | 4/2018 | Sherwood et al. |
| 2018/0336970 A1 | 11/2018 | Sherwood et al. |
| 2019/0025237 A1 | 1/2019 | Kelly et al. |
| 2019/0178827 A1 | 6/2019 | Schlichte et al. |
| 2019/0254538 A1 | 8/2019 | Erdman et al. |

(56) References Cited

U.S. PATENT DOCUMENTS

| | | |
|---|---|---|
| 2020/0124588 A1 | 4/2020 | Peterson et al. |
| 2020/0337566 A1 | 10/2020 | Peterson et al. |

FOREIGN PATENT DOCUMENTS

| | | |
|---|---|---|
| CN | 109270130 | 1/2019 |
| CN | 109310326 | 2/2019 |
| CN | 111801048 | 10/2020 |
| EP | 1764153 | 3/2007 |
| EP | 1806414 | 7/2007 |
| EP | 3093653 | 11/2016 |
| EP | 3210007 | 8/2017 |
| EP | 3431977 | 1/2019 |
| EP | 3439544 | 2/2019 |
| EP | 3755220 | 12/2020 |
| GB | 2523180 | 8/2015 |
| JP | 2019020415 | 2/2019 |
| KR | 20160000066 | 1/2016 |
| WO | 9947905 | 9/1999 |
| WO | 2001070114 | 9/2001 |
| WO | 2008088780 | 7/2008 |
| WO | 2009135070 | 11/2009 |
| WO | 2011102747 | 5/2011 |
| WO | 2011082178 | 7/2011 |
| WO | 2013090999 | 6/2013 |
| WO | 2013095730 | 6/2013 |
| WO | 2013189502 | 12/2013 |
| WO | 2015191558 | 12/2015 |
| WO | 2016064740 | 4/2016 |
| WO | 2016105464 | 6/2016 |
| WO | 2017218464 | 12/2017 |
| WO | 2018075731 | 4/2018 |
| WO | 2018213564 | 11/2018 |
| WO | 2019164925 | 8/2019 |
| WO | 2020081834 | 4/2020 |
| WO | 2020223208 | 11/2020 |

OTHER PUBLICATIONS

"International Search Report and Written Opinion," for PCT Application No. PCT/US2020/049395 dated Mar. 9, 2021 (17 pages).
"10 Leading Causes of Death, United States," (NCIPC) NCfIPaC. Web-based Injury Statistics Query and Reporting System. https://webappa.cdc.gov/sasweb/ncipc/leadcause.html, as available on Feb. 23, 2018 (3 pages).
Arasaradnam, R. P. et al., "Review Article: Next Generation Diagnostic Modalities in Gastroenterology—Gas Phase Volatile compound biomarker detection," Alimentary Pharmacology and Therapeutics 2014; 39: 780-789 (10 pages).
Banoei, Mohammad M. et al., "Metabolomics and Biomarker Discovery in Traumatic Brain Injury," Journal of Neurotrauma, vol. 35, No. 16, Mar. 2018 (59 pages).
Boots, Agnes W. et al., "The Versatile Use of Exhaled Volatile Organic Compounds in Human Health and Disease," J. Breath Res. 6 (2012) 027108 (21 pages).
Chen, Liangyou et al., "Diagnosis of Hemorrhage in a Prehospital Trauma Population Using Linear and Nonlinear Multiparameter Analysis of Vital Signs," 2007 Annual International Conference of the IEEE Engineering and Medicine and Biology Society, Aug. 22, 2007 (4 pages).
Chinopoulos, Christos "Which way Does the Citric Acid Cycle Turn During Hypoxia? The Critical Role of α-Ketoglutarate Dehydrogenase Complex," Journal of Neuroscience Research 91:1030-1043 (2013), 14 pages.
Chouchani, Edward T. et al., "Ischaemic Accumulation of Succinate Controls Reperfusion Injury Through Mitochondrial ROS," Nature. 2014; 515 (7527):431-435 (author manuscript), 29 pages.
"Communication Pursuant to Article 94(3) EPC," for European Patent Application No. 18180455.0 dated Feb. 11, 2019 (6 pages).
"Communication Pursuant to Rules 161(1) and 162 EPC," for European Patent Application No. 15790739.5 dated Jun. 1, 2017 (2 pages).

D'alessandro, Angelo et al., "Early Hemorrhage Triggers Metabolic Responses That Build Up During Prolonged Shock," Am J Physiol Regul Integr Comp Physiol 308: R1034-R1044, 2015 (11 pages).
D'alessandro, Angelo et al., "Plasma Succinate is a Predictor of Mortality in Critically Injured Patients," Journal of Trauma and Acute Care Surgery. 2017;83(3):491-495, Author manuscript (9 pages).
D'alessandro, Angelo et al., "Trauma/Hemorrhagic Shock Instigates Aberrant Metabolic Flux Through Glycolytic Pathways, as Revealed by Preliminary C-glucose Labeling Metabolomics," Journal of Translational Medicine 2015;13(1): 253 (14 pages).
Deen, David A. et al., "Graphene-Based Quantum Capacitance Wireless Vapor Sensors," IEEE Sensors Journal, vol. 14, No. 5, May 2014, pp. 1459-1466 (8 pages).
Droscher, S. et al., "Quantum Capacitance and Density of States of Graphene," Phys. Scr. T146 (2012) 014009, pp. 1-5 (5 pages).
Ebrish, M. A. et al., "Dielectric Thickness Dependence of Quantum Capacitance in Graphene Varactors with Local Metal Back Gates," Device Research Conference, 2012 (2 pages).
Ebrish, M. A. et al., "Operation of Multi-Finger Graphene Quantum Capacitance Varactors using Planarized Local Bottom Gate Electrodes," Applied Physics Letters, vol. 100, No. 14, Apr. 2012 (4 pages).
El Sayad, Mohamed et al., "Recent Advances of Hemorrhage Management in Severe Trauma," Emergency Medicine International, vol. 2014, Article ID 635956 (5 pages).
"European Search Report," for Dutch Patent Application No. 2019492 dated Apr. 12, 2018 (10 pages).
"European Search Report," for European Patent Application No. 18180455.0 dated Dec. 3, 2018 (5 pages).
"Fdc1004 4-Channel Capacitance-to-Digital Converter for Capacitive Sensing Solutions," Data Sheet SNOSCY5B Texas Instruments Aug. 2014—Revised 2015 (24 pages).
"Fdc1004evm User Guide," Literature No. SNAU163C, Texas Instruments Aug. 2014—Revised Oct. 2016 (46 pages).
"Final Office Action," for U.S. Appl. No. 14/883,895 dated Sep. 14, 2018 (16 pages).
"First Office Action," for Chinese Patent Application No. 201580056417.2 dated Feb. 11, 2019 (13 pages) with English summary.
Fisher, James P. et al., "Central Sympathetic Overactivity: Maladies and Mechanisms," Autonomic Neuroscience 148.1 (2009): 5-15 (11 pages).
Georgakilas, Vasilios et al., "Functionalization of Graphene: Covalent and Non-Covalent Approaches, Derivatives and Applications," Chemical Reviews, 2012, 14:112(11), pp. 6156-6214.
Goolsby, Craig et al., "Just-in-Time to Save Lives: A Pilot Study of Layperson Tourniquet Application," Academic Emergency Medicine, 2015;22(9):1113-1117 (5 pages).
Gutierrez, Guillermo et al., "Clinical Review: Hemorrhagic Shock," Critical Care 2004, 8:373-381 (9 pages).
Hill, Lisa J. et al., "Cystain D (CST5): An Ultra-Early Inflammatory Biomarker of Traumatic Brain Injury," Sci Rep. Jul. 10, 2017;7(1):5002 (10 pages).
Howard, Jt et al., "Reexamination of a Battlefield Trauma Golden Hour Policy," Journal of Trauma and Acute Care Surgery 2018;84(1): 11-18, Abstract only (2 pages).
Hu, Yuhai et al., "Chemically Functionalized Graphene and Their Applications in Electrochemical Energy Conversion and Storage," Advances in Graphene Science, Chapter 7, 2013, pp. 161-190 (30 pages).
"International Preliminary Report on Patentability," for PCT Application No. PCT/US2015/056243 dated May 4, 2017 (8 pages).
"International Preliminary Report on Patentability," for PCT Application No. PCT/US2018/037144 dated Dec. 27, 2018 (7 pages).
"International Preliminary Report on Patentability," for PCT Application No. PCT/US2019/018744 dated Sep. 3, 2020 (11 pages). 018744.
"International Search Report and Written Opinion," for PCT Application No. PCT/US2015/056243, dated Jan. 26, 2016 (12 pages).
"International Search Report and Written Opinion," for PCT Application No. PCT/US2017/037144 dated Oct. 6, 2017 (11 pages).

(56) References Cited

OTHER PUBLICATIONS

"International Search Report and Written Opinion," for PCT Application No. PCT/US2017/057318 dated Feb. 6, 2018 (14 pages).
"International Search Report and Written Opinion," for PCT Application No. PCT/US2018/033166 dated Oct. 2, 2018 (12 pages).
"International Search Report and Written Opinion," for PCT Application No. PCT/US2019/056766 dated Mar. 17, 2020.
"International Search Report and Written Opinion," for PCT Application No. PCT/US2019/018744 dated Jun. 28, 2019 (16 pages).
"International Search Report and Written Opinion," for PCT Application No. PCT/US2020/030223 dated Jul. 27, 2020 (17 pages).
"Invitation to Pay Additional Fees and, Where Applicable, Protest Fee," for PCT Application No. PCT/US2019/018744 dated May 7, 2019 (11 pages).
Kauvar, David S. et al., "Impact of Hemorrhage on Trauma Outcome: An Overview of Epidemiology, Clinical Presentations, and Therapeutic Considerations," Journal of Trauma and Acute Care Surgery, 2006;60(6): S3-S11 (9 pages).
Koester, Steven J. "Using the Quantum Capacitance in Graphene to Enable Varactors for Passive Wireless Sensing Applications," 2011 IEEE Sensors Proceedings, pp. 994-997, 2011 (4 pages).
Kotwal, Russ S. et al., "Eliminating Preventable Death on the Battlefield," Archives of Surgery 2011;146(12): 1350-1358 (9 pages).
Krausz, Michael M. "Initial Resuscitation of Hemorrhagic Shock," World Journal of Emergency Surgery 2006, 1:14 (5 pages).
Lexcen, D. R. et al., "Metabolomics Classifies Phase of Care and Identifies Risk for Mortality in a Porcine Model of Multiple Injuries and Hemorrhagic Shock," Journal of Trauma and Acute Care Surgery 2012;73(2):S147-S155, Abstract only (2 pages).
Li, Xiao et al., "Digital Health: Tracking Physiomes and Activity Using Wearable Biosensors Reveals Useful Health-Related Information," PLoS Biology 15.1 (2017): e2001402 (30 pages).
Lusczek, Elizabeth R. et al., "Assessment of Key Plasma Metabolites in Combat Casualties," Journal of Trauma and Acute Care Surgery. 2017;82(2):309-316 (8 pages).
Ma, Rui et al., "Acetone Sensing Using Graphene Quantum Capacitance Varactors," 2016 IEEE Sensors, Orlando, FL, 2016 (3 pages).
Magera, Mark J. et al., "Methylmalonic Acid Measured in Plasma and Urine by Stable-Isotope Dilution and Electrospray Tandem Mass Spectrometry," Clin Chem. Nov. 2000;46(11):1804-10 (7 pages).
"Mechanical Data," DGS (S-PDSO-G10) DSC0010B Package Outline, Example Board Layout, and Stencil Design. Texas Instruments 2016 (5 pages).
Murphy, Michael P. et al., "Krebs Cycle Reimagined: The Emerging Roles of Succinate and Itaconate as Signal Transducers," Cell, vol. 174, Issue 4, Aug. 9, 2018, pp. 780-784 (5 pages).
Nakhleh, Morad K. et al., "Diagnosis and Classification of 17 Diseases from 1404 Subjects via Pattern Analysis of Exhaled Molecules," ACS Nano 2017, 11, 112-125 (14 pages).
"Nano Mobile Healthcare Inc.," Company Profile on Reuters.com URL <http://www.reuters.com/finance/stocks/companyProfile?symbol=VNTH.PK> accessed Mar. 17, 2017 (2 pages).
"Non-Final Office Action," for U.S. Appl. No. 14/883,895 dated Apr. 30, 2018 (37 pages).
"Non-Final Office Action," for U.S. Appl. No. 14/883,895 dated Feb. 15, 2019 (17 pages).
Oprea, A. et al., "Integrated Temperature, Humidity and Gas Sensors on Flexible Substrates for Low-Power Applications," 007 IEEE Sensors, Atlanta, GA, 2007, pp. 158-161 (4 pages).
"Package Materials Information," Tape and Reel Information and Box Dimensions. Texas Instruments Feb. 13, 2016 (2 pages).
"Package Option Addendum," Packaging Information for FDC1004DGSR, DGST, DSCJ, DSCR and DSCT Devices. Texas Instruments May 2015 (2 pages).
"Partial File History," for U.S. Appl. No. 14/883,895, filed Nov. 15, 2015 to Feb. 5, 2020 (284 pages).
Rassaei, Liza et al., "Lactate Biosensors: Current Status and Outlook," Anal Bioanal Chem (2014) 406:123-137 (16 pages).
"Researchers Identify Inflammatory Biomarkers Indicating Brain Injury," University of Birmingham, posted Jul. 10, 2017 <https://www.birmingham.ac.uk/news/latest/2017/07/researchers-identify-inflammatory-biomarkers-indicating-brain-injury.aspx> (4 pages).
"Response to Advisory Action," dated Dec. 3, 2018, for U.S. Appl. No. 14/883,895, submitted via EFS-Web on Dec. 14, 2018, 11 pages.
"Response to Communication Pursuant to Rules 161(1) and 162 EPC," for European Patent Application No. 15790739.5 filed with the EPO dated Dec. 8, 2017 (14 pages).
"Response to Final Rejection," dated Sep. 14, 2018, for U.S. Appl. No. 14/883,895, submitted via EFS-Web on Nov. 7, 2018, 11 pages.
"Response to Non-Final Office Action," for U.S. Appl. No. 14/883,895, dated Apr. 30, 2018 and filed with the USPTO Jul. 2, 2018 (18 pages).
Russo, Matthew V. et al., "Inflammatory Neuroprotection Following Traumatic Brain Injury," Science. Aug. 19, 2016;353(6301):783-5 (4 pages).
Slaughter, Anne L. et al., "Glutamine Metabolism Drives Succinate Accumulation in Plasma and the Lung During Hemorrhagic Shock," Journal of Trauma and Acute Care Surgery. 2016;81(6):1012-1019 (8 pages).
"Standard Terms and Conditions for Evaluation Modules," Texas Instruments 2016 (5 pages).
Stewart, Ian J. et al., "The Potential Utility of Urinary Biomarkers for Risk Prediction in Combat Casualties: A Prospective Observational Cohort Study," Critical Care 2015;19(1):252 (8 pages).
Tripathi, Kumud M. et al., "Recent Advances in Engineered Graphene and Composites for Detection of Volatile Organic Compounds (VOCs) and Non-Invasive Diseases Diagnosis," Carbon 110 (2016)97-129 (34 pages).
Umbrello, Michele et al., "The Key Role of Nitric Oxide in Hypoxia: Hypoxic Vasodilation and Energy Supply-Demand Matching," Antioxidants and Redox Signaling, vol. 19, No. 14, Nov. 10, 2013 (22 pages).
Wang, David "FDC1004: Basics of Capacitive Sensing and Applications," Application Report SNOA927, Texas Instruments Dec. 2014 (12 pages).
Witowski, Nancy E. et al., "Metabolomic Analysis of Survival in Carbohydrate Pre-Fed Pigs Subjected to Shock and Polytrauma," Molecular BioSystems Apr. 26, 2016; 12(5), 34 pages.
Woodcock, Thomas et al., "The Role of Markers of Inflammation in Traumatic Brain Injury," Front Neurol. Mar. 4, 2013;4:18 (18 pages).
Invitation to Pay Additional Fees for PCT Application No. PCT/US2020/049395 dated Jan. 15, 2021 (13 pages).
"Communication Pursuant to Rule 164(2)(a) EPC," for European Patent Application No. 20775138.9 dated Apr. 18, 2023 (4 pages).
"Communication Pursuant to Rule 164(2)(b) and Article 94(3) EPC," for European Patent Application No. 20775138.9 dated Jun. 30, 2023 (9 pages).
"Response to Communication Pursuant to Rules 161(1) and 162 EPC," for European Patent Application No. 20775138.9 filed Oct. 27, 2022 (9 pages).
"First Office Action," for Chinese Patent Application No. 202080077847.3 dated Oct. 27, 2023 (15 pages) with English summary.
"Response to Communication Pursuant to Article 94(3) EPC," for European Patent Application No. 20775138.9 filed Nov. 9, 2023 (16 pages).

* cited by examiner

FLUID ANALYSIS SYSTEM

This application claims the benefit of U.S. Provisional Application No. 62/898,155, filed Sep. 10, 2019, the content of which is herein incorporated by reference in its entirety.

FIELD

Embodiments herein relate to a breath analysis system, and devices and methods related to the same.

BACKGROUND

The accurate detection of diseases can allow clinicians to provide appropriate therapeutic interventions. The early detection of diseases can lead to better treatment outcomes. Diseases can be detected using many different techniques including analyzing tissue samples, analyzing various bodily fluids, diagnostic scans, genetic sequencing, and the like.

Some disease states result in the production of specific chemical compounds. In some cases, volatile organic compounds (VOCs) released into a gaseous sample of a patient can be hallmarks of certain diseases. The detection of these compounds or differential sensing of the same can allow for the early detection of particular disease states.

SUMMARY

In a first aspect, a gas measurement device is included having a housing defining an interior volume. The housing can include a fluid ingress port, a fluid egress port, a bottom wall, and a circuit board disposed within the interior volume. The circuit board can include a first side and a second side, where the first side of the circuit board faces inward toward the interior volume. A plurality of gas sensors can be disposed on the first side of the circuit board and a plurality of conductive pads disposed on the second side of the circuit board, where a plurality of electrical contacts contact the conductive pads when the circuit board is seated within the housing.

In a second aspect, in addition to one or more of the preceding or following aspects, or in the alternative to some aspects, the gas sensors can include one or more graphene varactors.

In a third aspect, in addition to one or more of the preceding or following aspects, or in the alternative to some aspects, the gas measurement device can be further configured to be placed into electrical communication with a contact mount, the contact mount can include a plurality of electrical contacts disposed thereon and configured to be received through the bottom wall.

In a fourth aspect, in addition to one or more of the preceding or following aspects, or in the alternative to some aspects, the plurality of electrical contacts can include spring-loaded electrical contact pins.

In a fifth aspect, in addition to one or more of the preceding or following aspects, or in the alternative to some aspects, the interior volume can have a height between the circuit board and a lower border of the fluid ingress port, where the height is from 5 mm to 30 mm.

In a sixth aspect, in addition to one or more of the preceding or following aspects, or in the alternative to some aspects, where the plurality of gas sensors are positioned forming a pattern of higher density surrounding a central portion of the circuit board.

In a seventh aspect, in addition to one or more of the preceding or following aspects, or in the alternative to some aspects, the pattern of higher density can include a hollow shape surrounding a center of the interior volume.

In an eighth aspect, in addition to one or more of the preceding or following aspects, or in the alternative to some aspects, where more than 50% of a total number of gas sensors are placed at least 1 centimeter away from a central portion on the circuit board directly beneath a center of the fluid ingress port.

In a ninth aspect, in addition to one or more of the preceding or following aspects, or in the alternative to some aspects, where the fluid ingress port, the fluid egress port, and the interior volume can define a gas flow path, the gas flow path expanding in volume between the fluid ingress port and the fluid egress port.

In a tenth aspect, in addition to one or more of the preceding or following aspects, or in the alternative to some aspects, where the fluid egress port is shaped as a ring surrounding the fluid ingress port.

In an eleventh aspect, in addition to one or more of the preceding or following aspects, or in the alternative to some aspects, where the fluid egress port is shaped as a discontinuous ring surrounding the fluid ingress port.

In a twelfth aspect, in addition to one or more of the preceding or following aspects, or in the alternative to some aspects, the gas measurement device further can include a pressure operated valve in fluid communication with the fluid egress port, where the pressure operated valve opens when a pressure inside the interior volume is greater than 760 mm Hg.

In a thirteenth aspect, in addition to one or more of the preceding or following aspects, or in the alternative to some aspects, the gas measurement device further can include a one-way check valve in fluid communication with the fluid ingress port.

In a fourteenth aspect, in addition to one or more of the preceding or following aspects, or in the alternative to some aspects, the fluid ingress port can have an inner diameter of about 2 mm to 20 mm.

In a fifteenth aspect, in addition to one or more of the preceding or following aspects, or in the alternative to some aspects, the interior volume can have a volume of at least 50 $mm^3$ to 1000 $mm^3$.

In a sixteenth aspect, in addition to one or more of the preceding or following aspects, or in the alternative to some aspects, the circuit board of the gas measurement device further can include one or more heating elements.

In a seventeenth aspect, a gas measurement device is included having a housing defining an interior volume. The housing can include a fluid ingress port, a fluid egress port, and a circuit board disposed within the interior volume. The circuit board can include a first side and a second side, where the first side of the circuit board faces inward toward the interior volume. There can be a plurality of gas sensors disposed on the first side of the circuit board. The fluid ingress port can be disposed over a center of the interior volume, where the fluid egress port can be disposed between the center of the interior volume and a periphery of the interior volume.

In an eighteenth aspect, a method of analyzing a gas sample is included. The method can include passing a gas sample through a fluid ingress port into an interior volume defined by a housing, contacting the gas sample with gas sensors disposed in the interior volume and passing the gas sample out of the interior volume through a fluid egress port, where the fluid egress port surrounds the fluid ingress port.

In a nineteenth aspect, in addition to one or more of the preceding or following aspects, or in the alternative to some aspects, the method further can include heating the gas sample with heating elements inside the interior volume.

In a twentieth aspect, in addition to one or more of the preceding or following aspects, or in the alternative to some aspects, where the fluid ingress port, the fluid egress port, and the interior volume define a gas flow path, the gas flow path expanding in volume between the fluid ingress port and the fluid egress port.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
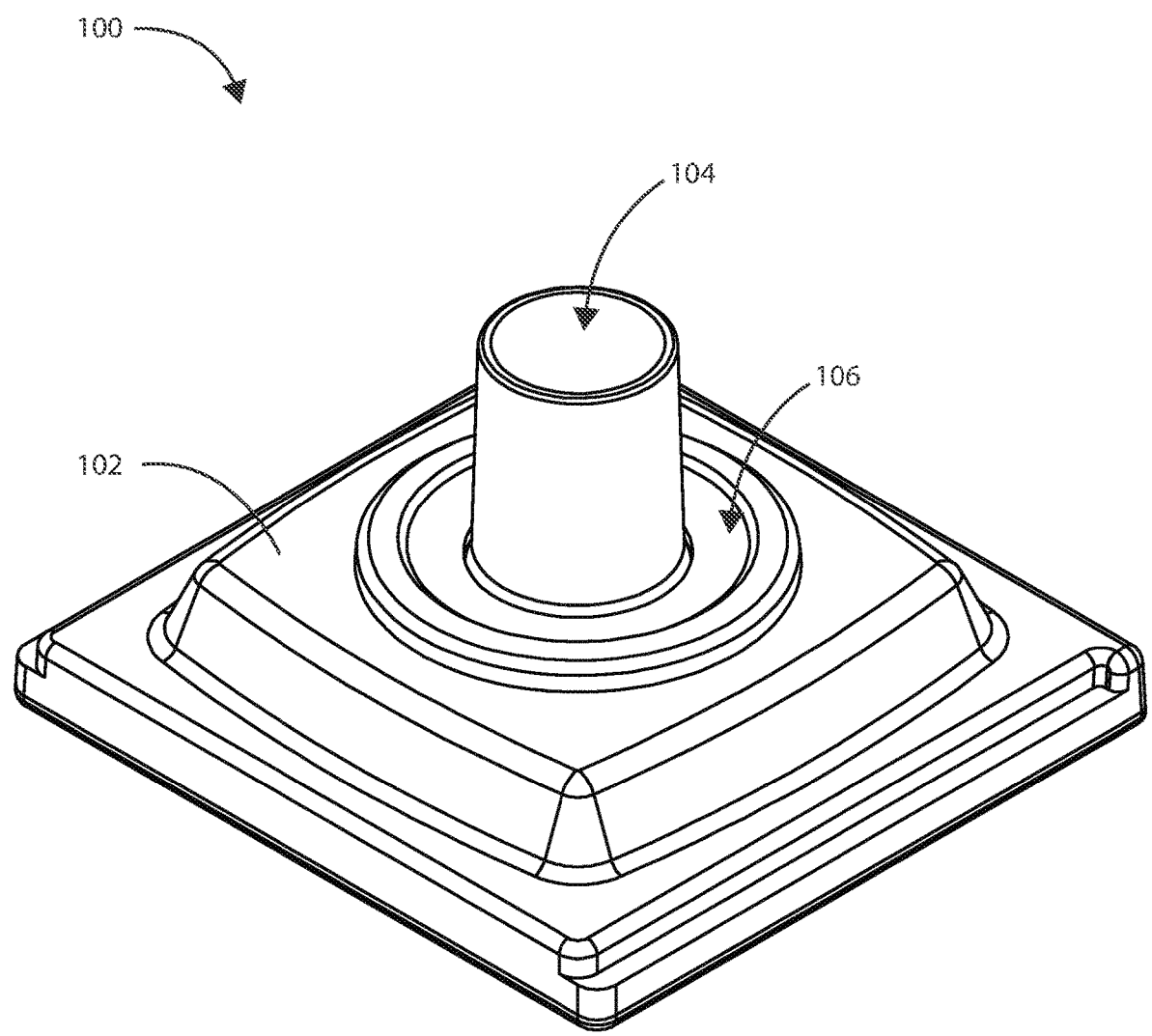
FIG. 1 is a perspective view of a gas measurement device in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Fluid analysis systems described herein includes a gas measurement device that can employ several different measurement methods to characterize the content of a gas sample. The gas measurement device is designed to have multiple gas sensors with similar or differing surface chemistry that can produce an electrochemical response to analytes present in a gas sample. The interaction between analytes present in a gas sample and a plurality of gas sensors can result in a unique sensor response for a particular mixture of gases in a sample. The response can be represented as a pattern or fingerprint of the gas sample. As the gaseous mixture changes, so does the pattern or fingerprint of that gas sample. Analysis of the signals from the gas sensors can allow for the detection of the health status of a subject including, but not limited to, the detection of various disease states.

In various embodiments, a gas measurement device is included having a housing defining an interior volume. The housing can include a fluid ingress port, a fluid egress port, and a bottom wall. The gas measurement device can also include a circuit board disposed within the interior volume, the circuit board comprising a first side and a second side. The first side of the circuit board can face inward toward the interior volume. A plurality of gas sensors can be disposed on the first side of the circuit board and a plurality of conductive pads disposed on the second side of the circuit board. The plurality of electrical contacts can contact the conductive pads when the circuit board is seated within the housing. This configuration can provide for a compact and efficient design allowing for electrical contacts which interface with the conductive pads for gathering signals from the gas sensors to engage with the second side of the circuit board away from the gas sensors.

In various embodiments, a gas measurement device is included having a housing defining an interior volume. The housing can include a fluid ingress port and a fluid egress port. The gas measurement device can further include a circuit board disposed within the interior volume, the circuit board comprising a first side and a second side. The first side of the circuit board faces inward toward the interior volume. A plurality of gas sensors can be disposed on the first side of the circuit board. The fluid ingress port can be disposed over a center of the interior volume. The fluid egress port can be disposed between the center of the interior volume and a periphery of the interior volume. This configuration can provide for advantageous flow characteristics of the sample gas over the gas sensors.

Referring now to FIG. 1, a perspective view of a gas measurement device 100 is shown in accordance with various embodiments herein. The gas measurement device 100 includes a housing 102. The housing 102 defines an interior volume (not shown in this view), which is discussed in more detail in reference to FIG. 3. The gas measurement device 100 includes a fluid ingress port 104. In various embodiments, the fluid ingress port 104 can be disposed over a center of the interior volume (described further below). The fluid ingress port 104 can be shaped as an oval, a circle, a triangle, a square, and the like. Materials suitable for use to create the housing can include, but are not to be limited to, one or more polymeric materials, metals, ceramics, composites, and the like.

The gas measurement device 100 includes a fluid egress port 106. In various embodiments, the fluid egress port 106 can surround the fluid ingress port 104. In various embodiments, the fluid egress port 106 can be shaped as an annular ring surrounding the fluid ingress port 104. In various embodiments, the fluid egress port 106 can be shaped as a discontinuous ring surrounding the fluid ingress port 104. In some embodiments, the gas measurement device 100 can include multiple fluid egress ports. In various embodiments, the fluid egress port 106 can be disposed between the center of the interior volume and a periphery of the interior volume. In some embodiments, the fluid egress port 106 can be disposed between the center of the interior volume and a periphery of the interior volume in a plane directly above the interior volume. In various embodiments, the fluid egress port 106 can have the same shape as the fluid ingress port 104 or a different shape than the fluid ingress port 104.

Figure 2:
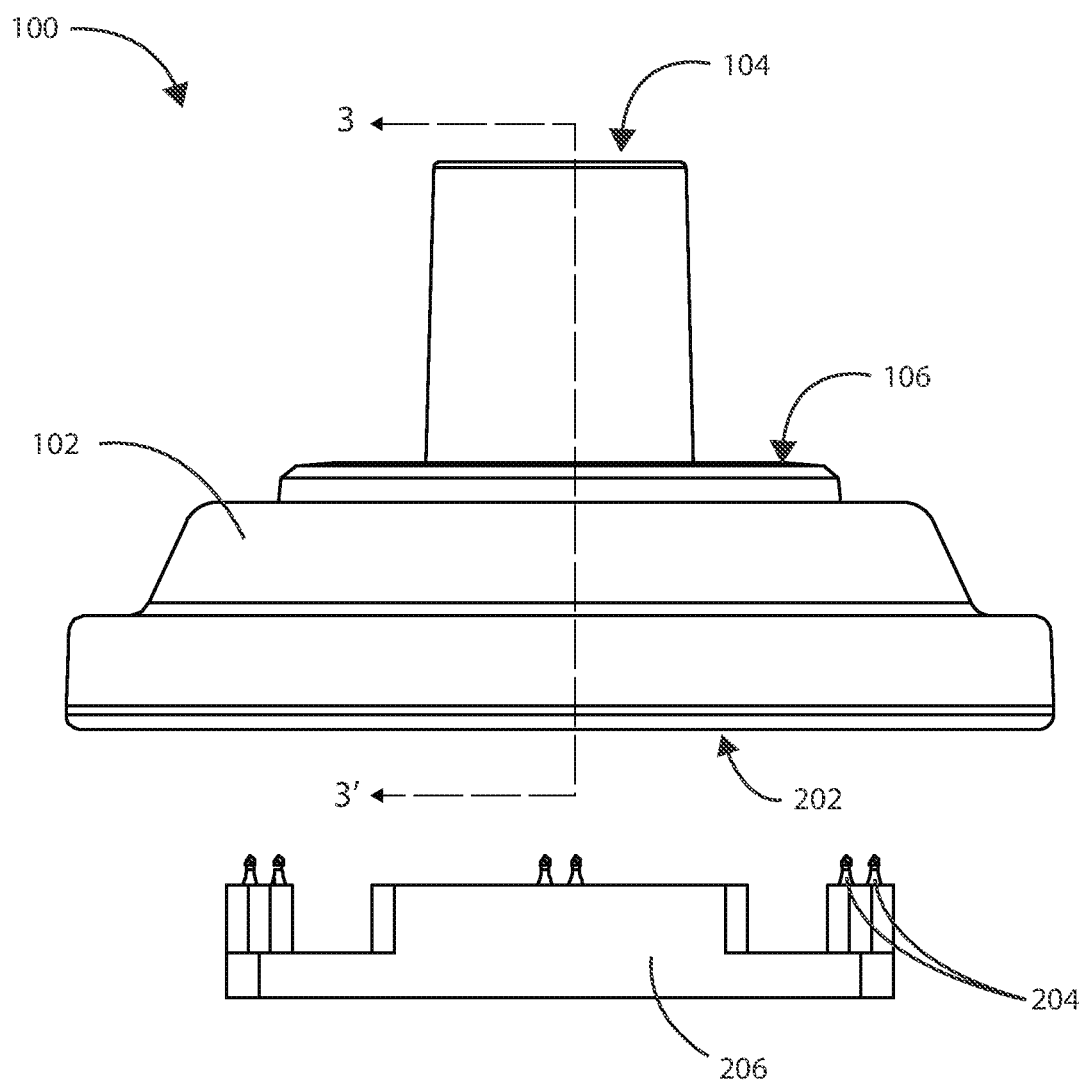
FIG. 2 is a side view of a gas measurement device in accordance with various embodiments herein.

Referring now to FIG. 2, a side view of a gas measurement device 100 is shown in accordance with various embodiments herein. The gas measurement device 100 includes a housing 102, a fluid ingress port 104, and a fluid egress port 106. The housing 102 defines an interior volume (not shown in this view), which is discussed in more detail in reference to FIG. 3. The gas measurement device 100 can include a bottom wall 202. In some embodiments, the bottom wall 202 spans the entire area at the bottom of the gas measurement device 100. In other embodiments, the bottom wall 202 spans just a portion of the area at the bottom of the gas measurement device 100. In various embodiments, the bottom wall can define one or more apertures configured to receive one or more of a plurality of electrical contacts 204, as discussed below.

In various embodiments, the gas measurement device 100 can be configured to be placed into electrical contact with a contact mount 206 having a plurality of electrical contacts 204 disposed thereon. The contact mount 206 can be in electrical communication with a reading and/or analysis device (not shown in this view). The bottom wall 202 can be configured to receive the plurality of electrical contacts 204 through the bottom wall 202. In some embodiments the bottom wall 202 can define one or more apertures configured to receive the plurality of electrical contacts 204. In various embodiments, the plurality of electrical contacts can include a plurality of electrical contact pins. In various embodiments, the plurality of electrical contacts can include a plurality of spring-loaded electrical contact pins.

Figure 3:
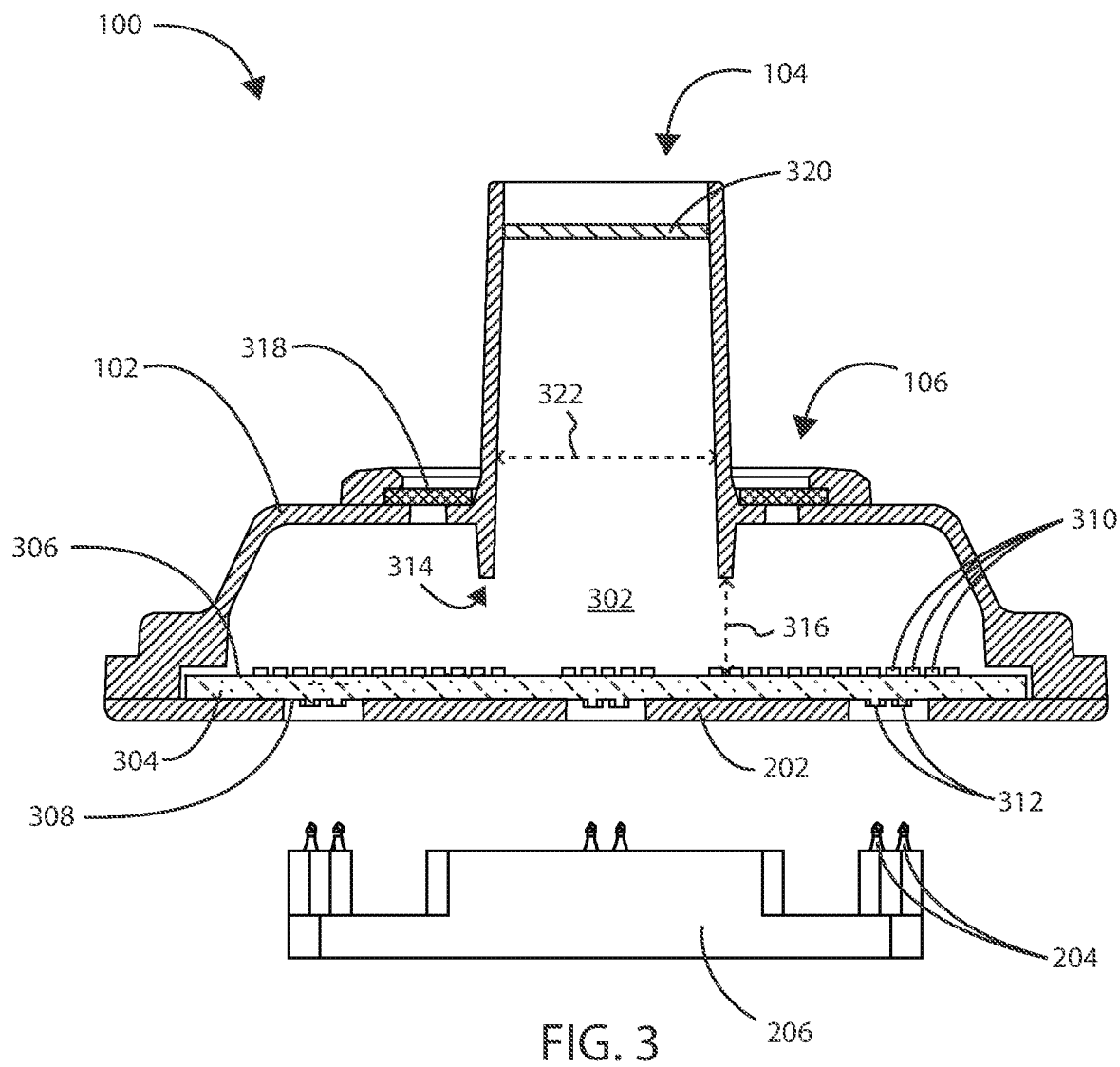
FIG. 3 is a cross-sectional view along line 3-3' of the gas measurement device of FIG. 2 in accordance with various embodiments herein.

Referring now to FIG. 3, a cross-sectional view along line 3-3' of the gas measurement device 100 of FIG. 2 is shown in accordance with various embodiments herein. The gas measurement device 100 includes a housing 102, a fluid ingress port 104, a fluid egress port 106, and a bottom wall 202. The housing 102 of gas measurement device 100 defines an interior volume 302. The fluid ingress port 104 includes a lower border 314 disposed within the interior volume 302. In various embodiments, the lower border 314 can extend within the interior volume 302 so as to shield the fluid egress port 106 and prevent a gas sample from immediate egress through the fluid egress port 106, thus directing a gas sample to flow first over the circuit board 304. In various embodiments, the interior volume 302, the lower border 314, and the housing 102 can define a gas flow path (described further below in reference to FIG. 8).

The fluid ingress port 104 can have an inner diameter 322 of various dimensions. In various embodiments, the inner diameter 322 of the fluid ingress port 104 can be from about 2 mm to 20 mm, such as at a portion of the fluid ingress port 104 bordering the interior volume 302 or at other portions of the fluid ingress port 104. In some embodiments, the inner diameter can be greater than or equal to 2 mm, 4 mm, 5 mm, 7 mm, 8 mm, or 10 mm. In some embodiments, the inner diameter can be less than or equal to 20 mm, 18 mm, 16 mm, 14 mm, 12 mm, or 10 mm. In some embodiments, the inner diameter can fall within a range of 2 mm to 20 mm, or 4 mm to 18 mm, or 5 mm to 16 mm, or 7 mm to 14 mm, or 8 mm to 12 mm, or can be about 10 mm. In some embodiments, the fluid ingress port 104 can have a constant diameter along a length of the fluid ingress port 104 from an exterior side to the interior volume 302. In other embodiments, the fluid ingress port 104 can have a varying diameter along a length of the fluid ingress port 104 from an exterior side to the interior volume 302.

In various embodiments where the fluid ingress port 104 is not circular, the fluid ingress port 104 can have a width greater than or equal to 2 mm, 4 mm, 5 mm, 7 mm, 8 mm, or 10 mm. In some embodiments, the width of a non-circular fluid ingress port 104 can be less than or equal to 20 mm, 18 mm, 16 mm, 14 mm, 12 mm, or 10 mm. In some embodiments, the width of a non-circular fluid ingress port 104 can fall within a range of 2 mm to 20 mm, or 4 mm to 18 mm, or 5 mm to 16 mm, or 7 mm to 14 mm, or 8 mm to 12 mm, or can be about 10 mm. In some embodiments, the fluid ingress port 104 can have a constant width along a length of the fluid ingress port 104 from an exterior side to the interior volume 302. In other embodiments, the fluid ingress port 104 can have a varying width along a length of the fluid ingress port 104 from an exterior side to the interior volume 302.

The interior volume 302 of the gas measurement device 100 can have various volumes. In various embodiments, the interior volume 302 can have a volume of at least 50 mm$^3$ to 1000 mm$^3$. In some embodiments, the volume can be greater than or equal to 50 mm$^3$, 140 mm$^3$, 230 mm$^3$, 320 mm$^3$, 410 mm$^3$, or 500 mm$^3$. In some embodiments, the volume can be less than or equal to 1000 mm$^3$, 900 mm$^3$, 800 mm$^3$, 700 mm$^3$, 600 mm$^3$, or 500 mm$^3$. In some embodiments, the volume can fall within a range of 50 mm$^3$ to 1000 mm$^3$, or 140 mm$^3$ to 900 mm$^3$, or 230 mm$^3$ to 800 mm$^3$, or 320 mm$^3$ to 700 mm$^3$, or 410 mm$^3$ to 600 mm$^3$, or can be about 500 mm$^3$.

The gas measurement device 100 further includes a circuit board 304 disposed within the interior volume 302 and seated within the housing 102. The circuit board 304 is disposed within the interior volume 302 such that it is in fluid communication with a fluid disposed within the interior volume 302. In various embodiments, the interior volume 302 of gas measurement device 100 can include a height 316 between the circuit board 304 and a lower border 314 of the fluid ingress port 104. In various embodiments, the circuit board 304 and housing 102 are configured such that the circuit board 304 can fit into the housing 102 in one orientation. In various other embodiments, the circuit board 304 and housing 102 are configured such that the circuit board 304 can fit into the housing 102 in more than one orientation.

In various embodiments, when the circuit board 304 is seated within the housing 102, the interior volume 302 can be substantially air tight such that fluid (other than small amounts that could leak) must pass through the fluid ingress port 104 and the fluid egress port 106 in order to pass through the interior volume. In some embodiments, the circuit board 304 can be seated within the housing 102 by fitting within two opposing parts of the housing 102. In some embodiments, the circuit board 304 can be seated within the housing 102 by way of a snap-fit or similar attachment mechanism. In some embodiments, the circuit board 304 can be seated within the housing 102 by way of a fastener, such as a screw, clip, bolt, attachment pin, or the like.

The height 316 between the circuit board 304 and a lower border 314 of the fluid ingress port 104 can be a height of various distances. In various embodiments, the height 316 can be from 5 mm to 30 mm. In some embodiments, the height can be greater than or equal to 5 mm, 8 mm, 11 mm, 14 mm, 17 mm, or 20 mm. In some embodiments, the height can be less than or equal to 30 mm, 28 mm, 26 mm, 24 mm, 22 mm, or 20 mm. In some embodiments, the distance can fall within a range of 5 mm to 30 mm, or 8 mm to 28 mm, or 11 mm to 26 mm, or 14 mm to 24 mm, or 17 mm to 22 mm, or can be about 20 mm.

The circuit board 304 includes a first side 306 and a second side 308. In various embodiments, the first side 306 of the circuit board 304 faces inward toward the interior volume 302 and the second side 308 of the circuit board 304 faces outward away from the interior volume 302. The circuit board 304 includes a plurality of gas sensors 310 and a plurality of conductive pads 312. In some embodiments, the plurality of gas sensors 310 can include a plurality of graphene varactors, while in other embodiments the plurality of gas sensors can include a single graphene varactor. In some embodiments, reference number 310 can represent chips or other structures on which one or more gas sensors and/or one or more graphene varactors are mounted. Exemplary gas sensors and graphene varactors will be discussed in more detail below. In various embodiments, the plurality of gas sensors 310 can be disposed on the first side 306 of the circuit board 304 and in fluid communication with a fluid disposed within the interior volume 302. In various embodiments, the fluid disposed within the interior volume 302 can include a gaseous breath sample.

In various embodiments, the plurality of conductive pads 312 can be disposed on the second side 308 of the circuit board 304. It will be appreciated that each gas sensor 310 disposed on the first side 306 of the circuit board 304 can be in electrical communication with at least one respective conductive pad 312 disposed on the second side 308 of the circuit board 304. In various embodiments, each gas sensor 310 disposed on the first side 306 of the circuit board 304 can be in electrical communication with at least two respective conductive pads 312 disposed on the second side 308 of the circuit board 304. The plurality of conductive pads 312 can be configured to be placed into electrical contact with a plurality of electrical contacts 204 disposed on a contact mount 206. Various configurations for the plurality of gas sensors 310 and the plurality of conductive pads 312 suitable for use with the embodiments herein will be discussed in more detail in reference to FIGS. 5 and 6.

In various embodiments, gas measurement device 100 also includes a pressure operated valve 318. The pressure operated valve 318 can be in fluid communication with the fluid egress port 106. In various embodiments, the pressure operated valve 318 can be a check valve. In various embodiments, the pressure operated valve 318 opens when a pressure inside the interior volume 302 is greater than 780 mm Hg. In other embodiments, the pressure operated valve 318 opens when a pressure inside the interior volume 302 is greater than 760 mm Hg. The pressure operated valve 318 can have a pressure threshold of various values. In some embodiments, the pressure threshold can be greater than or equal to 740 mmHg, 750 mmHg, 760 mmHg, 770 mmHg, 780 mmHg, 790 mmHg, or 800 mmHg, or can be an amount falling within a range between any of the foregoing. In some embodiments, it can be advantageous to maintain a positive pressure gradient between the interior volume 302 and the exterior environment.

The gas measurement device 100 can also include a one-way check valve 320 in fluid communication with the fluid ingress port 104 and interior volume 302. The one-way check valve 320 can allow a fluid to flow into the interior volume 302 of the gas measurement device while preventing backflow of a fluid from the interior volume 302 of the gas measurement device. In some embodiments, the one-way check valve 320 may be positioned farther upstream, such that it would not appear in this view of the gas measurement device 100. In some embodiments, the one-way check valve 320 can be omitted entirely.

Figure 4:
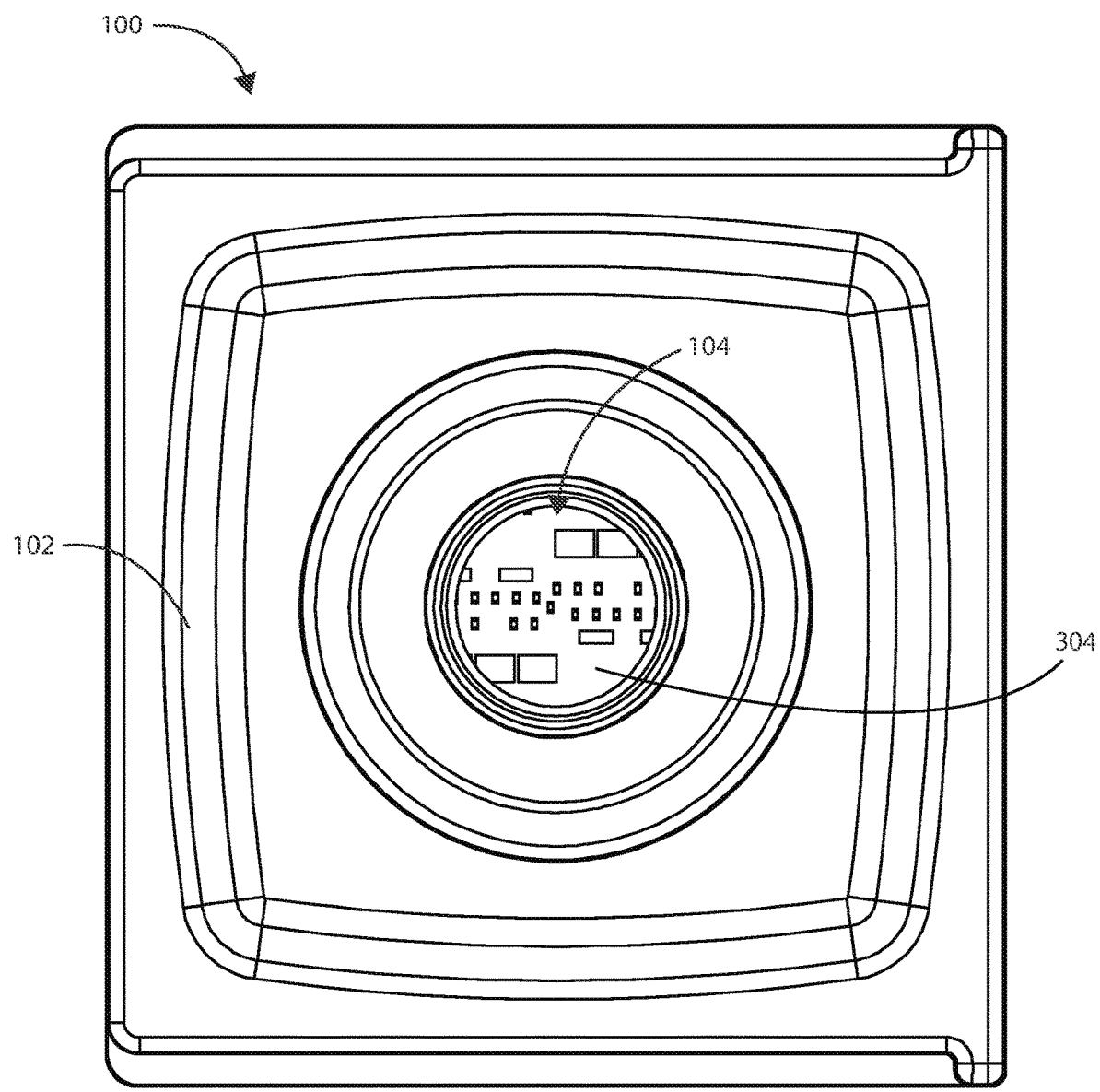
FIG. 4 is a top plan view of a gas measurement device in accordance with various embodiments herein.

Referring now to FIG. 4, a top-down view of a gas measurement device 100 is shown in accordance with various embodiments herein. The gas measurement device 100 includes a circuit board 304 seated within the housing 102 as seen through the fluid ingress port 104 (it will be appreciated that the one-way check valve 320 has been removed from the view in FIG. 4.).

Figure 5:
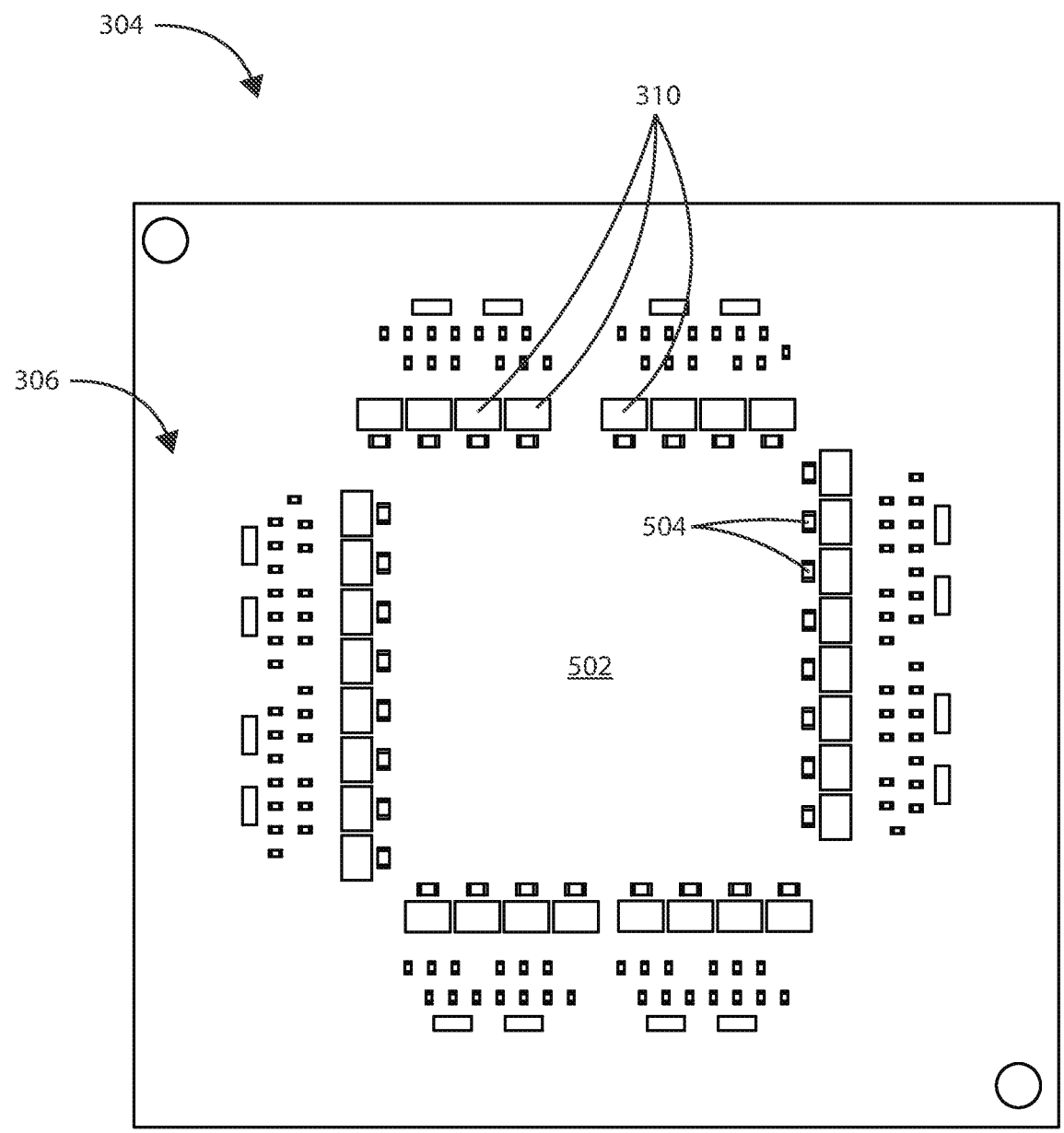
FIG. 5 is a top plan view of a circuit board in accordance with various embodiments herein.

Referring now to FIG. 5, a top-down view of a circuit board 304 is shown in accordance with various embodiments herein. The circuit board 304 includes a first side 306 having a plurality of gas sensors 310 disposed thereon. In various embodiments, the plurality of gas sensors 310 are positioned forming a pattern of higher density surrounding a central portion 502 of the first side 306 of circuit board 304. In some embodiments, the pattern of higher density can include a hollow shape surrounding a center of the interior volume 302. In various embodiments, the pattern of higher density can include a circle, an oval, or a polygon. It will be appreciated that while FIG. 5 does not show any gas sensors 310 disposed within the central portion 502, in some embodiments, one or more gas sensors 310 can be disposed within the central portion 502 of the first side 306. In various embodiments, circuit board 304 can further include one or more biometric sensors disposed on the first side 306 of the circuit board. Suitable biometric sensors can include, but are not to be limited to temperature sensors, pressure sensors, and humidity sensors.

While not intending to be bound by theory, it is believed that more vapor may condense on and/or water droplets may be deposited on or in the central portion 502. In some embodiments, condensed water and/or water droplets may adversely impact the gas sensors herein. As such, positioning the gas sensors generally away from the central portion 502 (or at least having a greater number of them away from the central portion 502) can offer advantages herein.

In various embodiments, more than 50% of the total number of gas sensors 310 can be placed at least 1 centimeter away from a central portion 502 on the circuit board 304 directly beneath a center of the fluid ingress port 104. In various embodiments, the circuit board 304 can include one or more heating elements 504. In various embodiments, the one or more heating elements 504 are positioned adjacent to each of the gas sensors 310. The one or more heating elements 504 can be used to heat the area around the gas sensors 310 or even the gas sensors 310 themselves to prevent condensation of water on a sensing surface of the gas sensors 310. Without being bound by any particular theory, it is believed that positioning the heating elements 504 to the periphery of the circuit board 304 can create a temperature differential between the periphery of the circuit board 304 and the central portion 502. The temperature differential can allow for the preferential condensation of moisture within the central portion 502 away from the surfaces of each of the gas sensors 310.

The heating elements 504 can heat the area around the gas sensors 310 and/or the gas sensors 310 themselves to temperatures to match the fluid within the interior volume 302 of the gas measurement device. In some embodiments, the gas sensors can be heated to a temperature that can be greater than or equal to 32° C., 33° C., 34° C., 35° C., 36° C., 37° C., 38° C., 39° C., 40° C., 41° C., or 42° C., or can be an amount falling within a range between any of the foregoing. In some embodiments, the temperature can fall within a range of 32° C. to 42° C., or 33° C. to 40° C., or 35° C. to 38° C., or can be about 37° C. In some embodiments the heating elements 504 can heat the area around the gas sensors 310 and/or the gas sensors 310 themselves to temperatures greater than the fluid within the interior volume 302 of the gas measurement device.

Figure 6:
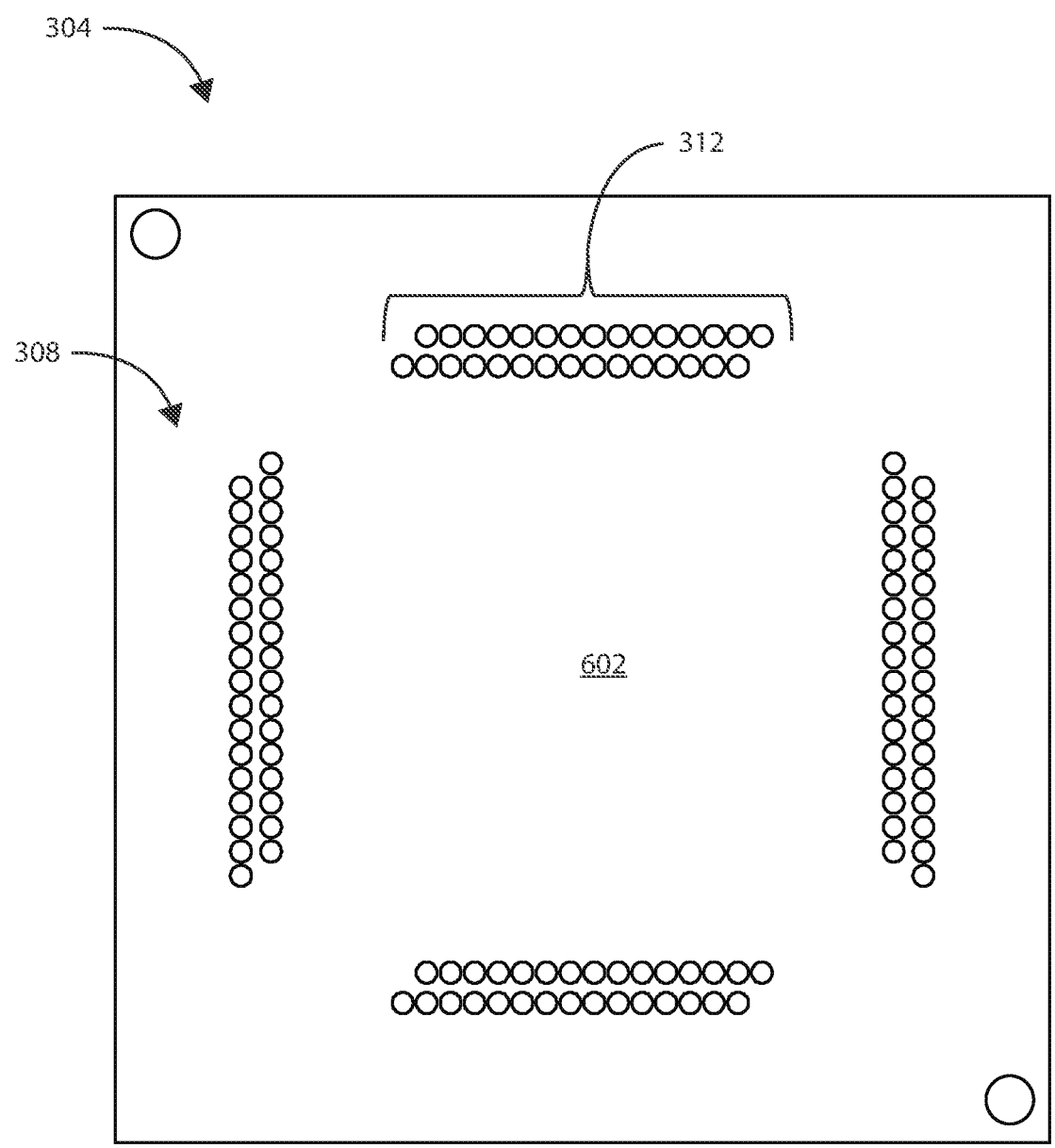
FIG. 6 is a bottom plan view of circuit board in accordance with various embodiments herein.

Referring now to FIG. 6, a bottom-up view of circuit board 304 is shown in accordance with various embodiments herein. The circuit board 304 includes a second side 308 having a plurality of conductive pads 312 disposed thereon. It will be appreciated that each gas sensor 310 disposed on the first side 306 of the circuit board 304 can be in electrical communication with at least one respective conductive pad 312 disposed on the second side 308 of the circuit board 304. In various embodiments, the plurality of conductive pads 312 are positioned forming a pattern of higher density surrounding a central portion 602 of the second side 308 of circuit board 304. In some embodiments, the pattern of higher density can include a hollow shape surrounding a central portion 602 of the second side 308 of circuit board 304 to match the pattern of higher density associated with the gas sensors 310 disposed on the first side 306 of the circuit board 304. In various embodiments, the pattern of higher density can include a circle, an oval, or a polygon. It will be appreciated that while FIG. 6 does not show any conductive pads 312 disposed within the central portion 602 of the second side 308, in some embodiments, one or more conductive pads 312 can be disposed within the central portion 602.

Figure 7:
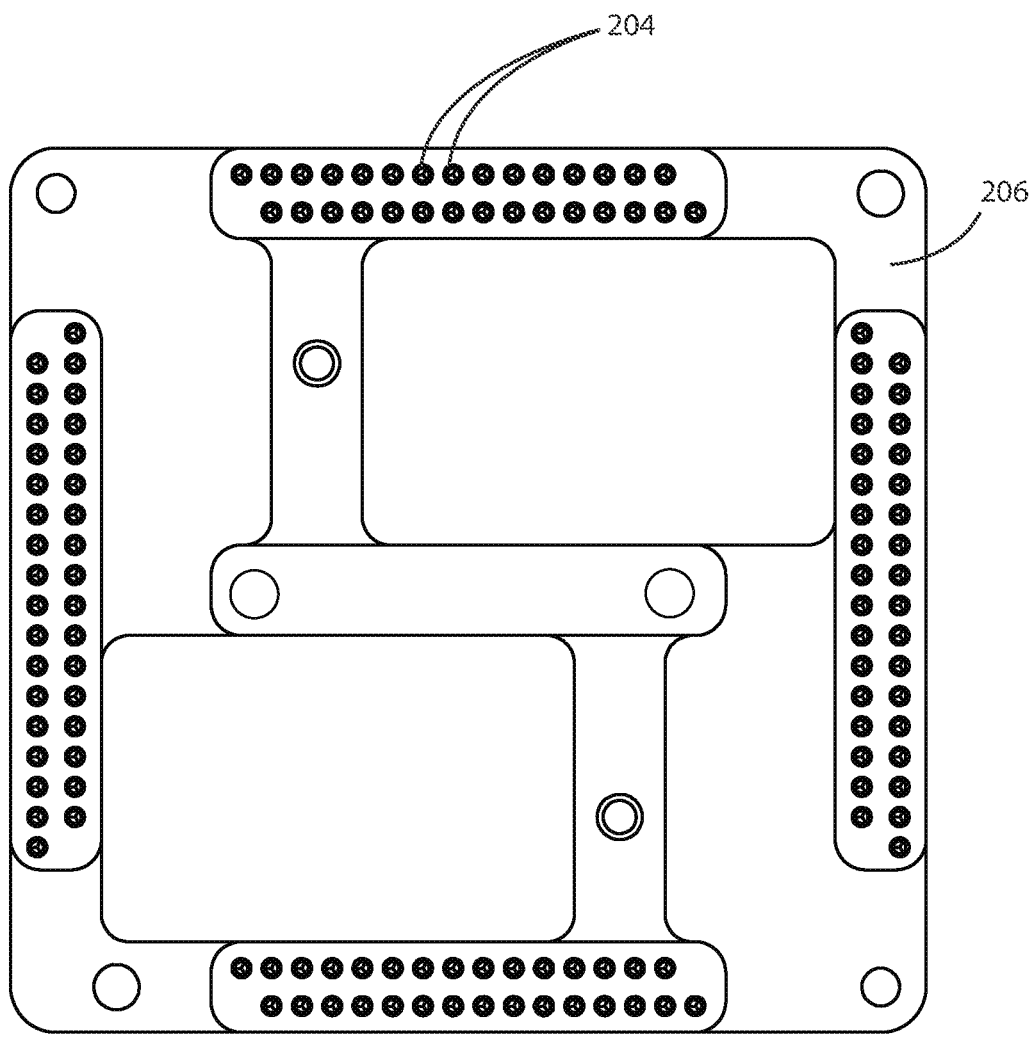
FIG. 7 is a top plan view of a contact mount in accordance with various embodiments herein.

Referring now to FIG. 7, a top-down view of a contact mount 206 is shown in accordance with various embodiments herein. The contact mount 206 can include a plurality of electrical contacts 204 disposed thereon. The contact mount 206 can be configured to be in electrical contact with the conducting pads 312 disposed on the second side 308 of the circuit board 304. The plurality of electrical contacts 204 can be configured to be received by the bottom wall 202 of the gas measurement device 100. In various embodiments, the plurality of electrical contacts 204 can be received through a corresponding plurality of apertures defined by the bottom wall 202 of the gas measurement device 100. In various embodiments, the plurality of electrical contacts 204 can include electrical contact pins. In various embodiments, the plurality of electrical contacts 204 can include spring-loaded electrical contact pins.

Figure 8:
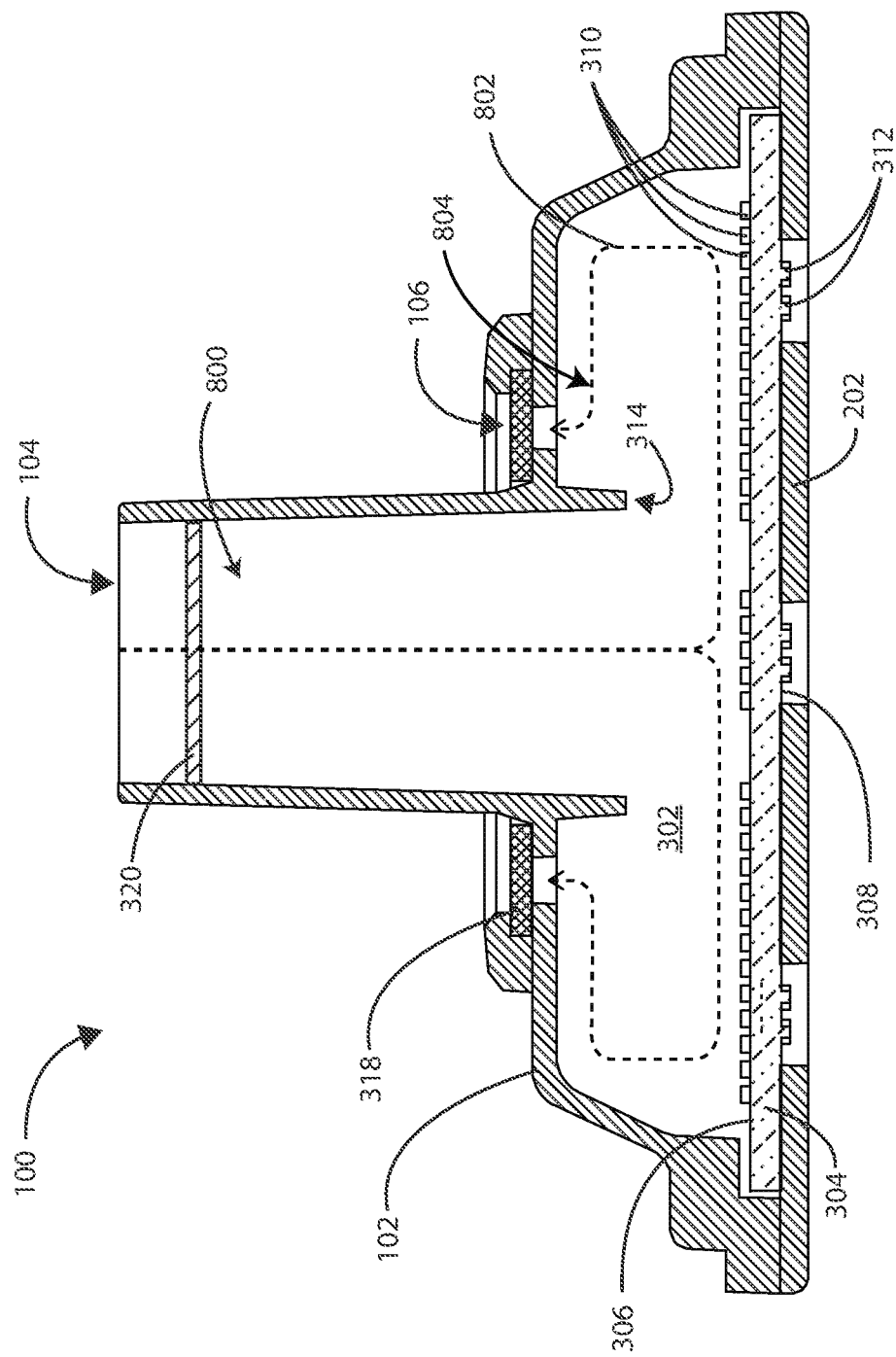
FIG. 8 is a schematic gas flow diagram within a cross-sectional view of a gas measurement device in accordance with various embodiments herein.
Figure 9:
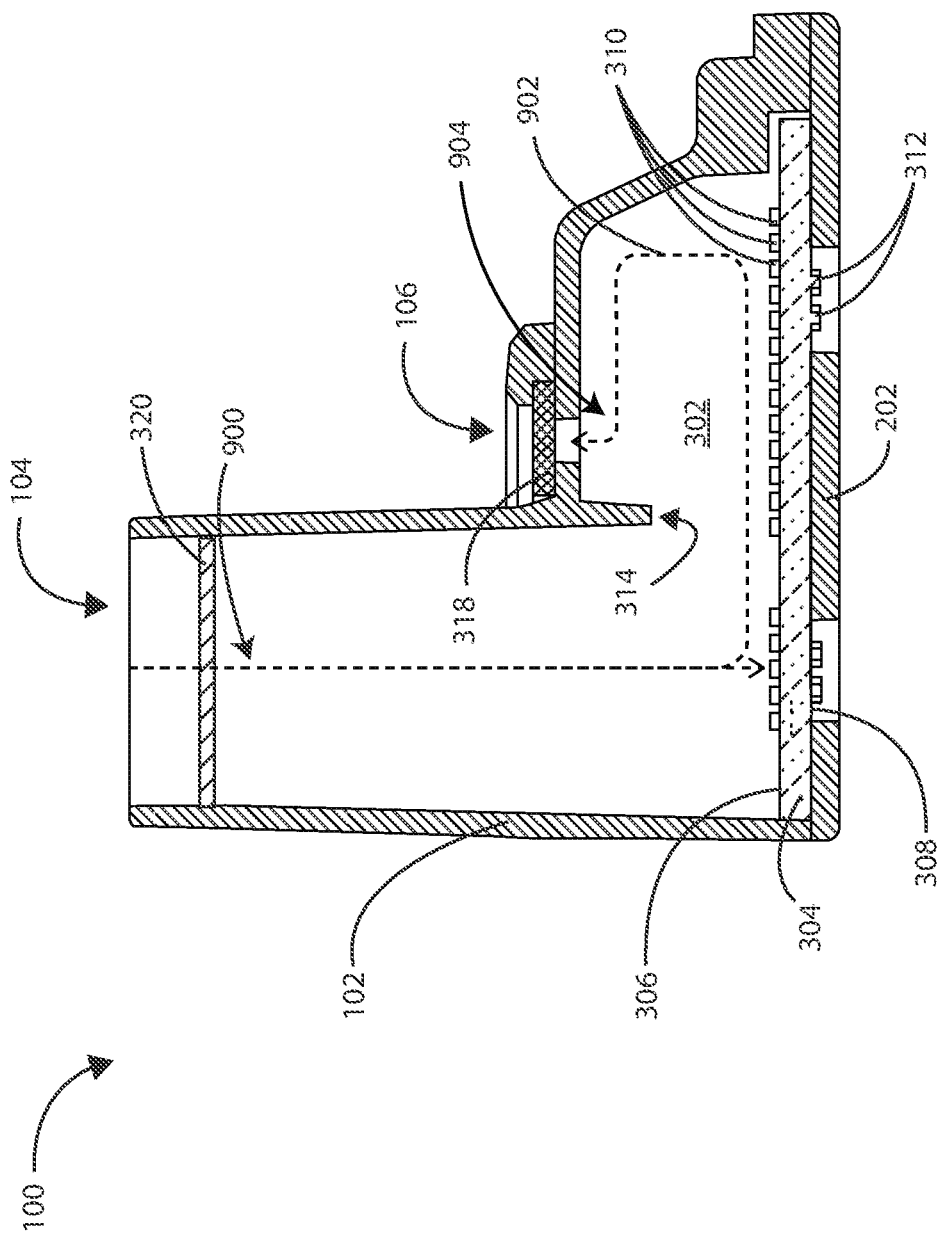
FIG. 9 is a schematic gas flow diagram within a cross-sectional view of an additional embodiment of a gas measurement device in accordance with various embodiments herein.

Referring now to FIGS. 8 and 9, the interior volume 302 defined by housing 102 can be configured to create a gas flow path configured to distribute a fluid across a plurality of gas sensors 310 disposed on a circuit board 304. In the embodiment shown in FIG. 8, a schematic gas flow diagram within a cross-sectional view of a gas measurement device 100 is shown in accordance with various embodiments herein. The gas measurement device 100 includes a housing 102, a fluid ingress port 104, a fluid egress port 106, a bottom wall 202, and a circuit board 304. The housing 102 of gas measurement device 100 defines an interior volume 302. The fluid ingress port 104 includes a lower border 314 disposed within the interior volume 302. The interior volume 302 is configured to be disposed adjacent the first side 306 of a circuit board 304.

The gas measurement device 100 is configured to create a substantially "W"-shaped gas flow path 802 in cross section. In various embodiments, the interior volume 302 can define the gas flow path 802. In various embodiments, the fluid ingress port 104, the fluid egress port 106, and the interior volume 302 define the gas flow path 802. The gas flow path 802 can expand in volume between the fluid ingress port 104 and the fluid egress port 106. In some embodiments, expansion of the gas flow path 802 can result in a reduction in pressure and/or a reduction in gas flow velocity. The gas flow path 802 can include a gas flow path beginning 800 and a gas flow path ending 804.

Without wishing to be bound by any particular theory, it is believed, that the gas sample can flow into the interior volume 302 of the gas measurement device and come into contact with circuit board 304 as it enters the interior volume 302 and spreads out across the surfaces of the gas sensors 310. The gas sample can follow the contours of the interior volume 302 as defined by the housing 102 and the lower border 314 and can be directed to exit through fluid egress port 106. The fluid egress port 106 can allow the gas sample to exit as a gas sample is being collected in the interior volume 302. In various embodiments, the gas sample is a breath sample that is exhaled by a subject into the interior volume 302. During inhalation by a subject, the flow of a gas sample in the housing 102 can remain stagnant and both the pressure operated valve 318 and the one-way check valve 320 can close. During exhalation, both the pressure operated valve 318 and the one-way check valve 320 can open allowing a breath sample to pass through the interior volume 302 contact the gas sensors and then pass out of the fluid egress port 106 with a transient positive pressure inside the interior volume 302 preventing ambient air from entering through the fluid egress port 106 into the interior volume 302 (e.g., preventing retrograde flow).

The gas measurement device 100 shown in FIG. 8 includes a circuit board 304 disposed within the interior volume 302 and seated within the housing 102. The circuit board 304 is disposed within the interior volume 302 such that it is in fluid communication with a fluid disposed within the interior volume 302. The circuit board 304 includes a first side 306 and a second side 308. In various embodiments, the first side 306 of the circuit board 304 faces inward toward the interior volume 302 and the second side 308 of the circuit board 304 faces outward away from the interior volume 302. The circuit board 304 includes a plurality of gas sensors 310 and a plurality of conductive pads 312. In some embodiments, the plurality of gas sensors 310 can include a plurality of graphene varactors. In various embodiments, the plurality of gas sensors 310 can be disposed on the first side 306 of the circuit board 304 and in fluid communication with a fluid disposed within the interior volume 302. In various embodiments, the fluid disposed within the interior volume 302 can include a breath sample. It will be appreciated that the gas measurement device 100 shown in FIG. 8 can be configured to be placed into electrical contact with a contact mount 206 having a plurality of electrical contacts 204 disposed thereon (contact mount not shown), as described elsewhere herein.

It will be appreciated that housings herein can take on many different shapes forming various flow paths. In the embodiment shown in FIG. 9, a schematic gas flow diagram within a cross-sectional view of an alternative embodiment of a gas measurement device 100 is shown in accordance with various embodiments herein. The gas measurement device 100 includes a housing 102, a fluid ingress port 104, a fluid egress port 106, a bottom wall 202, and a circuit board 304. The housing 102 of gas measurement device 100 defines an interior volume 302. The interior volume 302 is configured to be disposed adjacent the first side 306 of a circuit board 304.

The gas measurement device 100 is configured to create a "U"-shaped gas flow path 902. In various embodiments, the interior volume 302 can define the gas flow path 902. In various embodiments, the fluid ingress port 104, the fluid egress port 106, and the interior volume 302 define the gas flow path 902. The gas flow path 902 includes a gas flow path beginning 900 and a gas flow path ending 904.

It will be appreciated that the gas measurement device 100 shown in FIG. 9 represents an alternative for configuration of a gas measurement device in accordance with the various embodiments herein. Gas measurement device 100, as before, can include a circuit board 304 disposed within the interior volume 302 and seated within the housing 102. The circuit board 304 is disposed within the interior volume 302 such that it is in fluid communication with a fluid disposed within the interior volume 302. The circuit board 304 includes a first side 306 and a second side 308. In various embodiments, the first side 306 of the circuit board 304 faces inward toward the interior volume 302 and the second side 308 of the circuit board 304 faces outward away from the interior volume 302. The circuit board 304 includes a plurality of gas sensors 310 and a plurality of conductive pads 312. In some embodiments, the plurality of gas sensors 310 can include a plurality of graphene varactors. In various embodiments, the plurality of gas sensors 310 can be disposed on the first side 306 of the circuit board 304 and in fluid communication with a fluid disposed within the interior volume 302. In various embodiments, the fluid disposed within the interior volume 302 can include a breath sample. It will be appreciated that the gas measurement device 100 shown in FIG. 9 can be configured to be placed into electrical contact with a contact mount 206 having a plurality of electrical contacts 204 disposed thereon (contact mount not shown), as described elsewhere herein.

Methods

Many different methods are contemplated herein, including, but not limited to, methods of making, methods of using, and the like. Aspects of system/device operation described elsewhere herein can be performed as operations of one or more methods in accordance with various embodiments herein.

In an embodiment, a method of analyzing a gas sample is included. The method can include use of a gas measurement device as described elsewhere herein. The method can include passing a gas sample through a fluid ingress port into an interior volume as defined by a housing. The method can include contacting the gas sample with gas sensors disposed in the interior volume. The method can include passing the gas sample out of the interior volume through a fluid egress port, where the fluid egress port surrounds the fluid ingress port.

In an embodiment, the method can further include heating at least one of the gas sample, the gas sensors, and/or the area of the circuit board around the gas sensors, with heating elements inside the interior volume. In an embodiment of the method, the fluid ingress port, the fluid egress port, and the interior volume define a gas flow path. The gas flow path can define a "U" shape in cross section. In an embodiment of the method, the fluid ingress port, the fluid egress port, and the interior volume define a gas flow path, the gas flow path can define a "W" shape in cross section. In an embodiment of the method, the fluid ingress port, the fluid egress port, and the interior volume define a gas flow path, the gas flow path expanding in volume between the fluid ingress port and the fluid egress port.

In various embodiments herein, the methods can further include using one or more biometric sensors, such as temperature sensors, pressure sensors, and humidity sensors, to measure one or more biometric parameters including temperature, pressure, and humidity.

Gas Sensors

A variety of gas sensors are suitable for use in the gas measurement devices herein. In some embodiments, the gas sensors herein can be a part of and/or disposed on a chip component that can be mounted on a circuit board. In various embodiments, the chip can be affixed to the circuit board or can be a modular, removable component of the circuit board. The circuit boards suitable for use in the gas measurement devices herein can include an array of gas sensors about a central portion of the circuit board. The array can be arranged about the circuit board in any configuration, including a square configuration as shown in FIG. 5, a circle configuration, a rectangular configuration, and the like. The circuit board can include individual rows of gas sensors or it can include multiple rows of gas sensors within an array. In some embodiments, the array can be symmetric about a central portion of the circuit board. In other embodiments, the array can be asymmetric about the central portion of the circuit board.

In some embodiments, the circuit boards herein can include an array of gas sensors about a central portion of the circuit board, including 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 gas sensors, or can be an amount falling within a range between any of the foregoing. Electrical connections of the gas sensors to the circuit board can be accomplished with wire bonding, solder, or conductive epoxy using pads on both the circuit board and the gas sensors. In some embodiments, the gas sensors can be modular and removable from the circuit board. In some embodiments, each gas sensor can include one or more graphene varactors.

In various embodiments, each gas sensor can include one or more graphene varactors, including from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 graphene varactors, or can be an amount falling within a range between any of the foregoing. Electrical connections of the graphene varactors to the circuit board can be accomplished with wire bonding, solder, or conductive epoxy using pads on both the circuit board and the gas sensors. In some embodiments, the graphene varactors can be present on each gas sensor in an array.

In various embodiments, the circuit board can include from 20 to 160 graphene varactors disposed on an array of gas sensors. In some embodiments, the circuit board can include from 40 to 140 graphene varactors disposed on an array of gas sensors. In some embodiments, the circuit board can include from 60 to 120 graphene varactors disposed on an array of gas sensors. In yet other embodiments, the circuit board can include more than 120 graphene varactors disposed on an array of gas sensors.

A gas sensor array can be configured so several gas sensors are exposed to the flow of a complex gaseous mixture across the sensing surfaces of each gas sensor. Each sensing surface may be coated with chemical receptor elements that will have a binding specificity to certain chemical aspects of the target analytes. The gas sensor output signal can change as target analytes bind to the sensing receptors across the gas sensor surfaces. The electrical response to this binding can be recorded by measuring one or more of the electrical properties including capacitance, resistance, or inductance. The one or more electrical properties can be measured by an electrical connection system.

Figure 10:
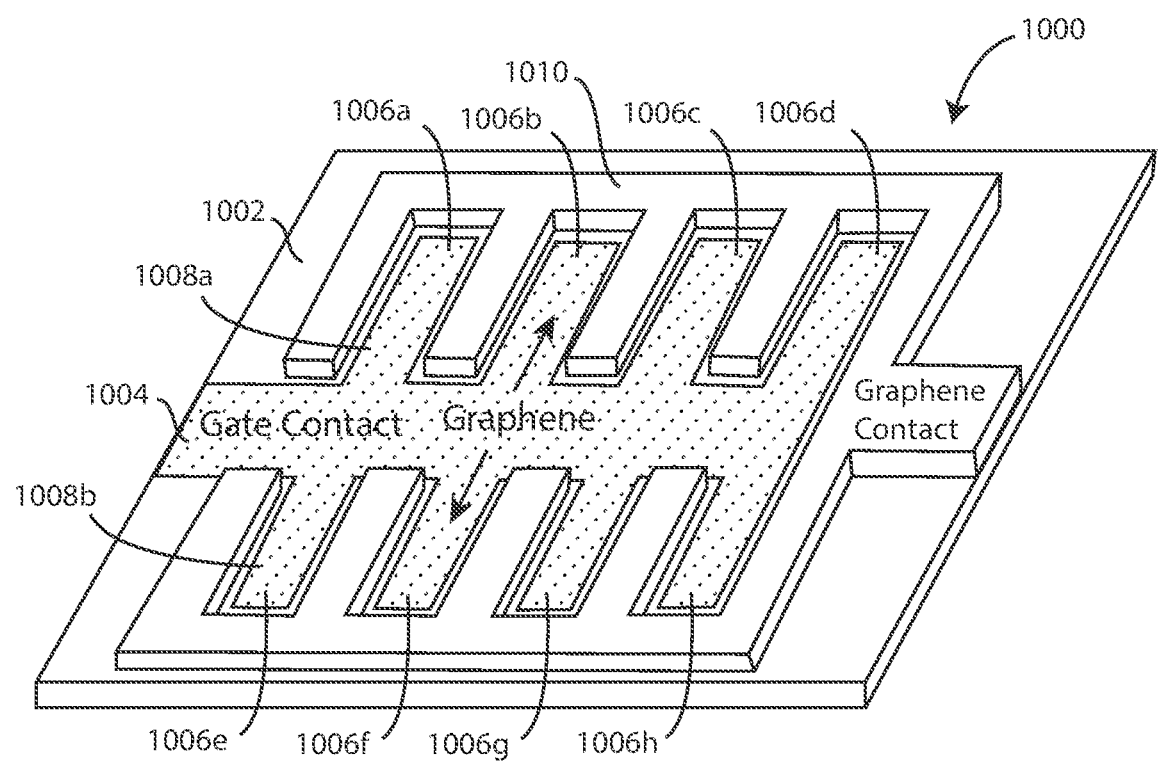
FIG. 10 is a schematic perspective view of a graphene varactor in accordance with various embodiments herein.

In various embodiments, the gas sensors herein can include graphene-based variable capacitors (or graphene varactors). However, in some embodiments, the gas sensors herein can be formed with other materials, such as borophene. Referring now to FIG. 10, a schematic view of a graphene varactor 1000 is shown in accordance with the embodiments herein. It will be appreciated that graphene varactors can be prepared in various ways with various geometries, and that the graphene varactor shown in FIG. 10 is just one example in accordance with the embodiments herein.

Each graphene varactor 1000 can include an insulator layer 1002, a gate electrode 1004 (or "gate contact"), a dielectric layer (not shown in FIG. 10), one or more graphene layers, such as graphene layers 1008a and 1008b, and a contact electrode 1010 (or "graphene contact"). In some embodiments, the graphene layer(s) 1008a-b can be contiguous, while in other embodiments the graphene layer(s) 1008a-b can be non-contiguous. Gate electrode 1004 can be deposited within one or more depressions formed in insulator layer 1002. Insulator layer 1002 can be formed from an insulative material, such as silicon dioxide, formed on a silicon substrate (wafer), and the like. Gate electrode 1004 can be formed by an electrically conductive material, such as chromium, copper, gold, silver, tungsten, aluminum, titanium, palladium, platinum, iridium, nickel, and any combinations or alloys thereof, which can be deposited on top of or embedded within the insulator layer 1002. The dielectric layer can be disposed on a surface of the insulator layer 1002 and the gate electrode 1004. The graphene layer(s) 1008a-b can be disposed on the dielectric layer. The dielectric layer will be discussed in more detail below in reference to FIG. 11.

Each graphene varactor 1000 can include eight gate electrode fingers 1006a-1006h. It will be appreciated that while graphene varactor 1000 shows eight gate electrode fingers 1006a-1006h, any number of gate electrode finger configurations can be contemplated. In some embodiments, an individual graphene varactor can include fewer than eight gate electrode fingers. In some embodiments, an individual graphene varactor can include more than eight gate electrode fingers. In other embodiments, an individual graphene varactor can include two gate electrode fingers. In some embodiments, an individual graphene varactor can include 1, 2, 3, 4, 5, 6, 7, 8, 9, 10, or more gate electrode fingers.

Each graphene varactor 1000 can include one or more contact electrodes 1010 disposed on portions of the graphene layers 1008a and 1008b. Contact electrode 1010 can be formed from an electrically conductive material, such as chromium, copper, gold, silver, tungsten, aluminum, titanium, palladium, platinum, iridium, nickel, and any combinations or alloys thereof. Further aspects of exemplary graphene varactors can be found in U.S. Pat. No. 9,513,244, the content of which is herein incorporated by reference in its entirety.

Figure 11:
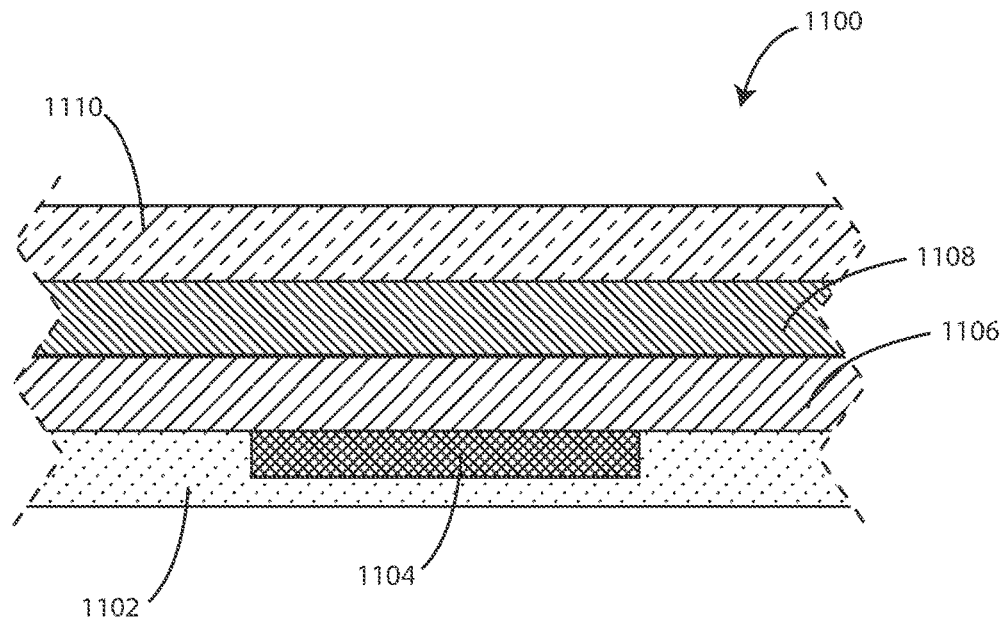
FIG. 11 is a schematic cross-sectional view of a portion of a graphene varactor in accordance with various embodiments herein.

Referring now to FIG. 11, a schematic cross-sectional view of a portion of a graphene varactor 1100 is shown in accordance with various embodiments herein. The graphene varactor 1100 can include an insulator layer 1102 and a gate electrode 1104 recessed into the insulator layer 1102. The gate electrode 1104 can be formed by depositing an electrically conductive material in the depression in the insulator layer 1102, as discussed above in reference to FIG. 10. A dielectric layer 1106 can be formed on a surface of the insulator layer 1102 and the gate electrode 1104. In some examples, the dielectric layer 1106 can be formed of a material, such as, silicon dioxide, aluminum oxide, hafnium dioxide, zirconium dioxide, hafnium silicate, or zirconium silicate.

The graphene varactor 1100 can include a single graphene layer 1108 that can be disposed on a surface of the dielectric layer 1106. The graphene layer 1108 can be surface-modified with a modification layer 1110. It will be appreciated that in some embodiments, the graphene layer 1108 is not surface-modified.

During use of the graphene varactors as described herein, a sweep performed on the excitation voltage of the entire gas measurement system provides data regarding the Dirac point (the voltage when the capacitance is at a minimum). As analytes are sensed by the graphene varactors, the voltage of the Dirac point can shift to a higher or lower value. The shape of the curve can also change. The changes in the sweep curve can be used as sensing features that can be attributed to the graphene varactor's response to the analyte/receptor interaction. Employing a fast sampling system while sweeping the voltage can provide kinetic information. Thus, the complete response can be measured at steady state, which can provide data related to how long it took to get to steady state (kinetic information).

The breath sensing systems described herein can include circuitry for generating signals from the discrete binding detectors. Such circuitry can include active and passive sensing circuits. Such circuitry can implement wired (direct electrical contact) or wireless sensing techniques.

Figure 12:
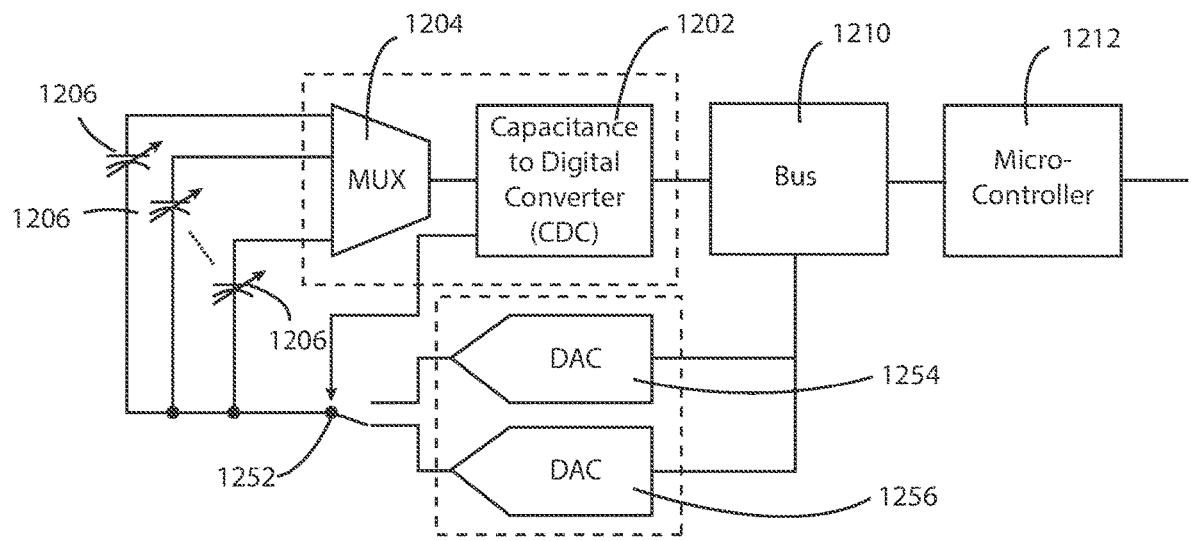
FIG. 12 is a schematic block diagram of circuitry to measure the capacitance of a plurality of graphene sensors in accordance with various embodiments herein.

Referring now to FIG. 12, a schematic diagram is shown of circuitry to measure the capacitance of a plurality of graphene sensors in accordance with another embodiment herein. The circuitry can include a capacitance to digital converter (CDC) 1202 in electrical communication with a multiplexor 1204. The multiplexor 1204 can provide selective electrical communication with a plurality of graphene varactors 1206. The connection to the other side of the graphene varactors 1206 can be controlled by a switch 1252 (as controlled by the CDC) and can provide selective electrical communication with a first digital to analog converter (DAC) 1254 and a second digital to analog converter (DAC) 1256. The other side of the DACs 1254, 1256 can be connected to a bus device 1210, or in some cases, the CDC 1202. In some embodiments, the bus device 1210 can interface with a microcontroller 1212 or other computing device.

In this case, the excitation signal from the CDC controls the switch between the output voltages of the two programmable Digital to Analog Converters (DACs). The programmed voltage difference between the DACs determines the excitation amplitude, providing an additional programmable scale factor to the measurement and allowing measurement of a wider range of capacitances than specified by the CDC. The bias voltage at which the capacitance is measured is equal to the difference between the bias voltage at the CDC input (via the multiplexor, usually equal to VCC/2, where VCC is the supply voltage) and the average voltage of the excitation signal, which is programmable. In some embodiments, buffer amplifiers and/or bypass capacitance can be used at the DAC outputs to maintain stable voltages during switching. Many different ranges of DC bias voltages can be used. In some embodiments, the range of DC bias voltages can be from −3 V to 3 V, or from −1 V to 1 V, or from −0.5 V to 0.5 V. Further aspects of exemplary sensing circuitry is provided in U.S. Publ. Pat. Appl. No. 2019/0025237, the content of which is herein incorporated by reference.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A gas measurement device comprising:
    a housing defining an interior volume,
    the housing comprising:
        a fluid ingress port;
        a fluid egress port;
        a bottom wall; and
    a circuit board disposed within the interior volume, the circuit board comprising a first side and a second side;
    wherein the first side of the circuit board faces inward toward the interior volume;
    a plurality of gas sensors disposed on the first side of the circuit board; and
    a plurality of conductive pads disposed on the second side of the circuit board;
    wherein a plurality of electrical contacts contact the conductive pads when the circuit board is seated within the housing;
    the gas measurement device configured to be placed into electrical communication with a contact mount, the contact mount comprising a plurality of electrical contacts disposed thereon and configured to be received through the bottom wall.

2. The gas measurement device of claim 1, wherein the gas sensors comprise one or more graphene varactors.

3. The gas measurement device of claim 1, wherein the plurality of electrical contacts comprise spring-loaded electrical contact pins.

4. The gas measurement device of claim 1, wherein the interior volume has a height between the circuit board and a lower border of the fluid ingress port, wherein the height is from 5 mm to 30 mm.

5. The gas measurement device of claim 1, wherein the plurality of gas sensors are positioned forming a pattern of higher density surrounding a central portion of the circuit board.

6. The gas measurement device of claim 5, wherein the pattern of higher density comprises a hollow shape surrounding a center of the interior volume.

7. The gas measurement device of claim 1, wherein more than 50% of a total number of gas sensors are placed at least 1 centimeter away from a central portion on the circuit board directly beneath a center of the fluid ingress port.

8. The gas measurement device of claim 1, wherein the fluid ingress port, the fluid egress port, and the interior volume define a gas flow path, the gas flow path expanding in volume between the fluid ingress port and the fluid egress port.

9. The gas measurement device of claim 1, wherein the fluid egress port is shaped as a ring surrounding the fluid ingress port.

10. The gas measurement device of claim 1, wherein the fluid egress port is shaped as a discontinuous ring surrounding the fluid ingress port.

11. The gas measurement device of claim 1, further comprising a pressure operated valve in fluid communication with the fluid egress port, wherein the pressure operated valve opens when a pressure inside the interior volume is greater than 760 mm Hg.

12. The gas measurement device of claim 1, further comprising a one-way check valve in fluid communication with the fluid ingress port.

13. The gas measurement device of claim 1, wherein the fluid ingress port has an inner diameter of 2 mm to 20 mm.

14. The gas measurement device of claim 1, wherein the interior volume has a volume of at least 50 mm$^3$ to 1000 mm$^3$.

15. A gas measurement device comprising:
    a housing defining an interior volume,
    the housing comprising:
        a fluid ingress port;
        a fluid egress port;
        a bottom wall; and
    a circuit board disposed within the interior volume, the circuit board comprising a first side and a second side;
    wherein the first side of the circuit board faces inward toward the interior volume;
    a plurality of gas sensors disposed on the first side of the circuit board; and
    a plurality of conductive pads disposed on the second side of the circuit board;
    wherein a plurality of electrical contacts contact the conductive pads when the circuit board is seated within the housing; and wherein more than 50% of a total number of gas sensors are placed at least 1 centimeter away from a central portion on the circuit board directly beneath a center of the fluid ingress port.

16. A gas measurement device comprising:
a housing defining an interior volume,
the housing comprising:
  a fluid ingress port;
  a fluid egress port;
  a bottom wall; and
a circuit board disposed within the interior volume, the circuit board comprising a first side and a second side;
wherein the first side of the circuit board faces inward toward the interior volume;
a plurality of gas sensors disposed on the first side of the circuit board; and
a plurality of conductive pads disposed on the second side of the circuit board;
wherein a plurality of electrical contacts contact the conductive pads when the circuit board is seated within the housing; and
wherein the fluid egress port is shaped as a ring surrounding the fluid ingress port.

* * * * *